US011872141B2

(12) United States Patent
Lee et al.

(10) Patent No.: US 11,872,141 B2
(45) Date of Patent: Jan. 16, 2024

(54) SYSTEM AND METHOD FOR A MEDICAL IMPLANT WITH INTEGRATED PROPULSORS

(71) Applicants: Randall F. Lee, Southlake, TX (US); Ian A. Lee, Carrollton, TX (US)

(72) Inventors: Randall F. Lee, Southlake, TX (US); Ian A. Lee, Carrollton, TX (US)

(*) Notice: Subject to any disclaimer, the term of this patent is extended or adjusted under 35 U.S.C. 154(b) by 0 days.

(21) Appl. No.: 18/196,755

(22) Filed: May 12, 2023

(65) Prior Publication Data

US 2023/0277332 A1 Sep. 7, 2023

Related U.S. Application Data

(63) Continuation of application No. PCT/US2022/077928, filed on Oct. 11, 2022.

(60) Provisional application No. 63/393,220, filed on Jul. 28, 2022, provisional application No. 63/254,810, filed on Oct. 12, 2021.

(51) Int. Cl.
*A61F 2/28* (2006.01)
*A61F 2/46* (2006.01)
*A61F 2/30* (2006.01)
*A61B 17/86* (2006.01)
*A61B 17/00* (2006.01)
*A61B 17/68* (2006.01)

(52) U.S. Cl.
CPC .............. *A61F 2/46* (2013.01); *A61F 2/28* (2013.01); *A61F 2/30771* (2013.01); *A61B 17/861* (2013.01); *A61B 17/864* (2013.01); *A61B 17/8635* (2013.01); *A61B 2017/00862* (2013.01); *A61B 2017/00867* (2013.01); *A61B 2017/681* (2013.01); *A61F 2002/30777* (2013.01)

(58) Field of Classification Search
CPC ............ A61B 17/8004; A61B 17/8014; A61B 17/8095; A61B 17/84; A61B 17/823; A61B 2017/681; A61B 17/7216; A61B 17/7225; A61B 17/8023; A61F 2/30734; A61F 2002/30736; A61F 2002/4223; A61F 2002/4212; A61F 2/28; A61F 2002/30995; A61F 2/447
See application file for complete search history.

(56) References Cited

U.S. PATENT DOCUMENTS

| | | | | |
|---|---|---|---|---|
| 6,629,998 | B1 * | 10/2003 | Lin | A61F 2/447 |
| | | | | 623/17.11 |
| 6,824,564 | B2 * | 11/2004 | Crozet | A61B 17/86 |
| | | | | 623/17.11 |
| 7,214,232 | B2 * | 5/2007 | Bowman | A61B 17/068 |
| | | | | 606/232 |

(Continued)

FOREIGN PATENT DOCUMENTS

RU 2029520 C1 2/1995

OTHER PUBLICATIONS

Communication Relating to the Results of the Partial International Search; dated Jan. 27, 2023, by the ISA/EP, re PCT/US2022/077928.

(Continued)

*Primary Examiner* — Alvin J Stewart
(74) *Attorney, Agent, or Firm* — Law Office of Bill Naifeh

(57) ABSTRACT

Disclosed are embodiments of medical implants containing an integrated propulsor system. Additionally, methods of insertion are also disclosed.

19 Claims, 15 Drawing Sheets

(56) References Cited

U.S. PATENT DOCUMENTS

| | | | |
|---|---|---|---|
| 7,922,765 B2 | 4/2011 | Reiley | |
| 8,585,742 B2* | 11/2013 | Windolf | A61B 17/7028 606/257 |
| 9,017,412 B2* | 4/2015 | Wolters | A61F 2/442 606/296 |
| 9,039,765 B2 | 5/2015 | Trieu | |
| 9,662,158 B2 | 5/2017 | Reiley | |
| 9,931,141 B2 | 4/2018 | Jimenez | |
| 9,956,013 B2 | 5/2018 | Reiley et al. | |
| 10,376,367 B2* | 8/2019 | Fallin | A61B 17/8004 |
| 11,134,997 B2 | 10/2021 | Vrionis et al. | |
| 11,234,830 B2 | 2/2022 | Mesiwala et al. | |
| 2007/0038219 A1 | 2/2007 | Matthis et al. | |
| 2007/0156241 A1 | 7/2007 | Reiley et al. | |
| 2007/0276388 A1* | 11/2007 | Robertson | A61B 17/064 606/75 |
| 2008/0103598 A1 | 5/2008 | Trudeau et al. | |
| 2010/0003638 A1 | 1/2010 | Collins et al. | |
| 2012/0265301 A1* | 10/2012 | Demers | A61B 17/8872 606/301 |
| 2013/0172888 A1 | 7/2013 | Necuze | |
| 2015/0038969 A1 | 2/2015 | Garcia et al. | |
| 2016/0089138 A1* | 3/2016 | Early | A61B 17/0642 606/75 |
| 2016/0113770 A1* | 4/2016 | Early | A61F 2/30 623/23.39 |
| 2016/0192930 A1* | 7/2016 | Finley | A61B 17/15 606/75 |
| 2016/0228257 A1* | 8/2016 | Predick | A61B 17/8061 |
| 2016/0256203 A1* | 9/2016 | Gephart | A61B 17/808 |
| 2017/0000537 A1* | 1/2017 | Fallin | A61B 17/808 |
| 2017/0252036 A1* | 9/2017 | Palmer | A61B 17/8685 |
| 2018/0214192 A1 | 8/2018 | Roby et al. | |
| 2019/0090922 A1* | 3/2019 | Bluchel | A61B 17/8095 |
| 2019/0298528 A1 | 10/2019 | Lindsey et al. | |
| 2020/0129214 A1 | 4/2020 | Pepper et al. | |
| 2020/0261240 A1 | 8/2020 | Mesiwala et al. | |
| 2022/0008220 A1* | 1/2022 | Coyne | A61F 2/30734 |
| 2022/0133488 A1* | 5/2022 | Dewey | A61F 2/442 623/17.16 |
| 2022/0175551 A1* | 6/2022 | Castro | A61F 2/4455 |
| 2023/0000631 A1* | 1/2023 | Ginn | A61B 17/1664 |
| 2023/0000639 A1* | 1/2023 | Stuart | A61F 2/4603 |

OTHER PUBLICATIONS

International Search Report, dated Mar. 20, 2023, by the ISA/EP, re PCT/US2022/077928.

Written Opinion, dated Mar. 20, 2023, by the ISA/EP, re PCT/US2022/077928.

* cited by examiner

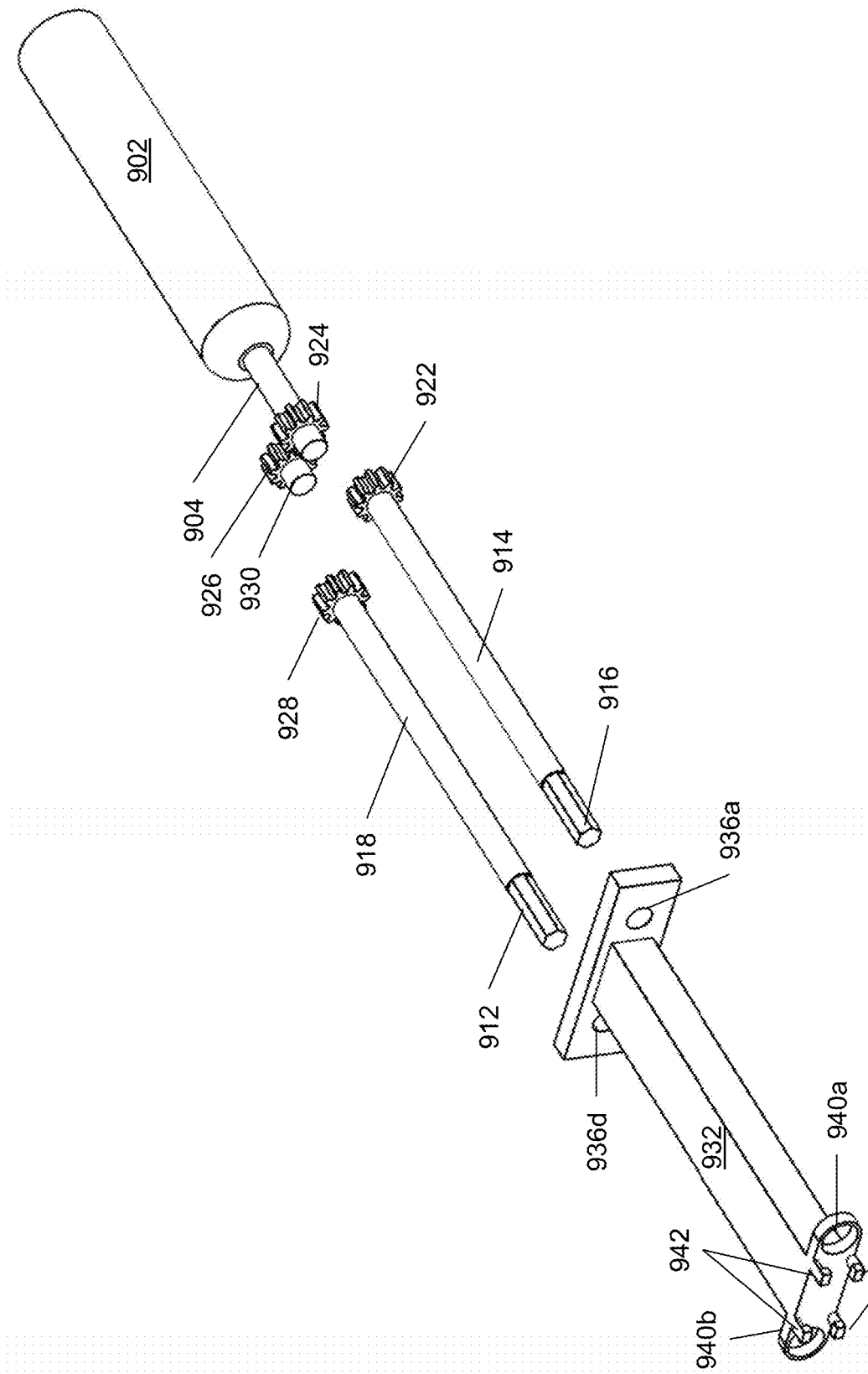

SYSTEM AND METHOD FOR A MEDICAL IMPLANT WITH INTEGRATED PROPULSORS

CROSS REFERENCE TO RELATED APPLICATIONS

This application is a continuation of International Application No. PCT/US2022/077928, filed Oct. 11, 2022, entitled "System and Method for a Medical Implant with Integrated Propulsors," which claims the benefit of the filing date of U.S. Provisional Application No. 63/393,220, filed Jul. 28, 2022, entitled "Systems and Methods of Boney Compression, Fixation, and Fusion Apparatus with Integrated Propulsor," and claims the benefit of the filing date of U.S. Provisional Application No. 63/254,810, filed Oct. 12, 2021, entitled "Systems and Methods of Boney Compression, Fixation, and Fusion Apparatus with Integrated Propulsor," the disclosures of which are incorporated herein by reference for all purposes.

TECHNICAL FIELD

The invention relates in general to fixation and/or fusion surgically implanted medical devices. In particular, the invention relates to medical implantable devices with one or more integrated propulsors.

BACKGROUND INFORMATION

Over the years orthopedic surgeons have developed numerous implants and tools for joining boney structures together. Such fixation or joining is desirable when the boney structure is broken due to trauma or iatrogenic action. In other situations, it may be desirable to join two boney structures together to relieve nerve impingement or other medical conditions.

In many situations, boney structures are joined with medical implants which must be positioned and secured by applying impact forces. In certain situations, impact forces may cause further damage or trauma. Furthermore, the placement of an implant via impact forces may not be precise.

What is needed, therefore, is a medical implant or implantable device which does not rely solely on impact forces for positioning and placement.

SUMMARY

In response to these and other problems, in one embodiment, there is a medical implant comprising of one or more self-contained propulsors to position the implant within one or more boney structures. In certain embodiment, there may be a surgical implant comprising: a chassis comprising, a main body positioned along a longitudinal axis; a first arm extending laterally from a side of the main body having a first bearing aperture defined therein; a second arm extending laterally from the main body on an opposing side of the main body, the second arm having a second bearing aperture defined therein; a first propulsor comprising, a first longitudinal shaft having a first rotational axis; a clockwise auger flight positioned about a portion of the first longitudinal shaft, a first smooth bearing portion of the first longitudinal shaft; wherein the first smooth bearing portion fits within the first bearing aperture; wherein the first longitudinal shaft is positioned a first lateral distance from the main body of the chassis such that a rotation of the clockwise auger flight clears the main body; a second propulsor comprising, a second longitudinal shaft having a second rotational axis; a counter-clockwise auger flight positioned about a portion of the second longitudinal shaft, a second smooth bearing portion of the second longitudinal shaft; wherein the second smooth bearing portion fits within the second bearing aperture; and wherein the second longitudinal shaft is positioned a second lateral distance from the main body of the chassis such that a rotation of the counter-clockwise auger flight clears the main body.

Certain embodiments may include the above embodiments, wherein the chassis further comprises: a third arm extending laterally from the main body having a third bearing aperture defined therein; a fourth arm extending laterally from the main body having a fourth bearing aperture defined therein and extending in opposite direction from the third arm; wherein the first bearing aperture is linearly aligned with the third bearing aperture and the second bearing aperture is linearly aligned with the fourth bearing aperture; a third smooth bearing portion on the first shaft of the first propulsor, wherein the third smooth bearing portion fits within the third bearing aperture; and a fourth smooth bearing portion on the second shaft of the second propulsor, wherein the fourth smooth bearing portion fits within the fourth bearing aperture.

Certain embodiments may include the above embodiments, wherein the main body comprises a cage having a distal face and a proximal face, wherein the distal face defines an aperture for receiving bone tissue.

Certain embodiments may include the above embodiments, wherein the distal face comprises at least one member having a distal face which is shaped to cut through boney tissue during positioning.

Certain embodiments may include the above embodiments, wherein the main body comprises a cage having at least one side aperture for receiving bone tissue from a cutting action of at least one propulsor.

Certain embodiments may include the above embodiments, wherein the main body comprises a flexible region that can be biased before implantation to actively compress boney tissue after implantation.

Certain embodiments may include the above embodiments, wherein the flexible region is formed from an elastomeric material.

Certain embodiments may include the above embodiments, wherein the flexible region is formed from a shape memory alloy.

Certain embodiments may include the above embodiments, wherein the flexible region is a mechanical linkage.

Certain embodiments may include the above embodiments, wherein the chassis is fenestrated to encourage bone growth after placement.

Certain embodiments may include the above embodiments, wherein the chassis is cannulated.

Certain embodiments may include the above embodiments, wherein each propulsor comprises a distal end and a proximal end and the distal end is pointed to cut through boney tissue during positioning.

Certain embodiments may include the above embodiments, wherein each propulsor comprises a distal end and a proximal end and the distal end including a cutting surface to cut through boney tissue during positioning.

Certain embodiments may include the above embodiments, wherein each propulsor comprises a distal end and a proximal end and the proximal end includes a torque engagement feature.

Certain embodiments may include the above embodiments, wherein each propulsor comprises a distal end and a proximal end, wherein the distal end includes a forward distal thread-form shape to assist in drilling through boney tissue during implant positioning.

Certain embodiments may include the above embodiments, wherein the longitudinal axis of the first shaft of the first propulsor and the longitudinal axis of the second shaft of the second propulsor intersect at a common point forward to the implant.

Certain embodiments may include the above embodiments, wherein the longitudinal axis of the first shaft of the first propulsor and the longitudinal axis of the second shaft of the second propulsor intersect at a common point behind the implant.

Certain embodiments may include the above embodiments, wherein each propulsor is fenestrated to encourage bone growth after placement.

Certain embodiments may include the above embodiments, wherein each propulsor is cannulated.

Embodiments of the present invention may also include an insertion instrument for a surgical implant, comprising: a torque inducer having a distal and proximal end, an actuating shaft having a distal end and proximal end wherein the distal end of the torque inducer is fixedly coupled to the proximal end of the actuating shaft, a first secondary drive shaft having a proximal end and a distal end; a second secondary drive shaft having a proximal end and a distal end; and a drive train coupled to the distal end of the actuating shaft and coupled to the proximal end of the first secondary drive shaft and coupled to the proximal end of the second secondary drive shaft such that when the actuating shaft is rotated in a first direction, the first secondary drive shaft is rotated in an opposite direction and the second secondary drive shaft is rotated in the first direction.

Certain embodiments of the insertion instrument may include embodiments wherein the torque inducer comprises an elongated handle having a rotational axis aligned with a longitudinal axis of the actuating shaft.

Certain embodiments of the insertion instrument may include embodiments wherein the drive train comprises: a first spur gear fixedly coupled to a distal end portion of the actuating shaft; a second spur gear coupled to a proximal portion of the first secondary drive shaft, the second spur gear is in a first tooth meshing engagement with the first spur gear such that when the first spur gear rotates in a first rotational direction, the second spur gear rotates in a second rotational direction; a third spur gear coupled to an idler drive shaft, the third spur gear is in a second tooth meshing engagement with the first spur gear such that when the first spur gear rotates in the first rotational direction, the third spur gear rotates in the second rotational direction; and a fourth spur gear coupled to the second secondary drive shaft, the fourth spur gear is in a third tooth meshing engagement with the third spur gear such that when the third spur gear rotates in the second rotational direction, the fourth spur gear rotates in the first rotational direction.

Embodiments of the present invention may also include a method of joining two boney structures together using a surgical implant, the method comprising: rotating a first propulsor of the surgical implant about the first propulsor's longitudinal axis in a first rotational direction within a first boney structure to propel an implant in a first longitudinal direction; rotating a second propulsor of the surgical implant about the second propulsor's longitudinal axis in an opposing rotational direction within a second boney structure to propel an implant in the first longitudinal direction; harvesting bone tissue from a distal side of the surgical implant into a retaining cavity of the surgical implant as the surgical implant is propelled forward, and harvesting bone tissue from at least one lateral side of the surgical implant into the retaining cavity as the surgical implant is propelled forward.

Additional embodiments of the above method may further comprising compacting the harvested bone tissue within the retaining cavity as the surgical implant is propelled forward.

Additional embodiments of the above method may further comprising compressing the first boney structure towards the second boney structure as the surgical implant is propelled in the first longitudinal direction.

Embodiments of the present invention may also include a method of joining two boney structures together using a surgical implant, the method comprising: laterally biasing a first propulsor of the surgical implant with respect to a second propulsor of the surgical implant; stabilizing the biasing of the first propulsor with respect to the second propulsor during implantation and positioning; rotating the first propulsor of the surgical implant about the first propulsor's longitudinal axis in a first rotational direction within a first boney structure to propel an implant in a first longitudinal direction; rotating a second propulsor of the surgical implant about the second propulsor's longitudinal axis in an opposing rotational direction within a second boney structure to propel an implant in the first longitudinal direction; and removing the stabilizing such that the first boney structure is laterally compressed against the second boney structure.

Embodiments of the present invention may also include a method of joining two boney structures together using a surgical implant, the method comprising: inducing a rotation in an actuating shaft; rotating a first secondary shaft in a first rotational direction as a result of rotating the actuating shaft; rotating a second secondary shaft in a second rotational direction as a result of rotating the actuating shaft; rotating a first propulsor of the surgical implant about the first propulsor's longitudinal axis in a first rotational direction within a first boney structure as a result of rotating the first secondary shaft; rotating a second propulsor of the surgical implant about the second propulsor's longitudinal axis in a second rotational direction within a second boney structure to propel an implant in the first longitudinal direction; and propelling the surgical implant in a longitudinal direction as a result of rotating the first propulsor in a first rotational direction and rotating the second propulsor in a second rotational direction.

Additional embodiments of the above method may further comprising: harvesting bone tissue from a distal side of the surgical implant into a retaining cavity of the surgical implant as the surgical implant is propelled in the first longitudinal direction, and harvesting bone tissue from at least one lateral side of the surgical implant into the retaining cavity as the surgical implant is propelled in the first longitudinal direction.

Additional embodiments of the above method may further comprising compacting the harvested bone tissue within the retaining cavity as the surgical implant is propelled in the first longitudinal direction.

These and other features, and advantages, will be more clearly understood from the following detailed description taken in conjunction with the accompanying drawings. It is important to note the drawings are not intended to represent the only aspect of the invention. The features and advantages of the present disclosure will be readily apparent to those skilled in the art. While numerous changes may be made by those skilled in the art, such changes are within the spirit of the invention.

BRIEF DESCRIPTION OF THE DRAWINGS

FIG. 9C is a perspective view of the exploded insertion instrument of FIG. 9A from a distal perspective.

DETAILED DESCRIPTION

Figure 1A:
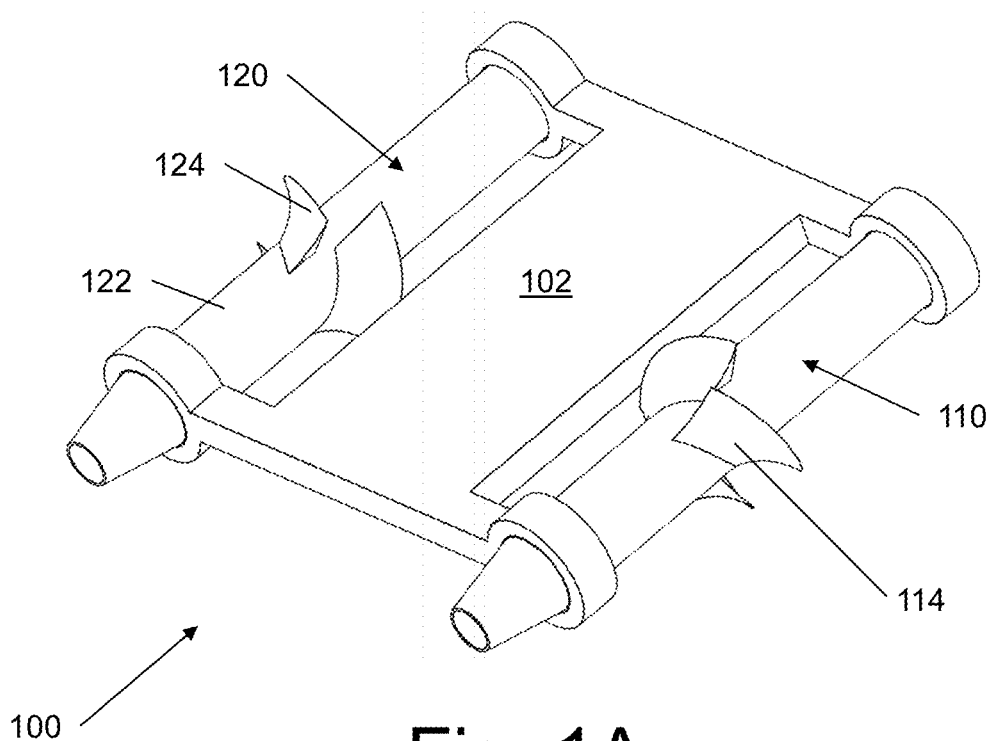
FIG. 1A is a perspective view of one embodiment of a medical implant.

For the purposes of promoting an understanding of the principles of the present inventions, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

When directions, such as upper, lower, top, bottom, clockwise, counter-clockwise, are discussed in this disclosure, such directions are meant to only supply reference directions for the illustrated figures and for orientation of components in respect to each other or to illustrate the figures. The directions should not be read to imply actual directions used in any resulting invention or actual use. Under no circumstances, should such directions be read to limit or impart any meaning into the claims.

Figure 1B:
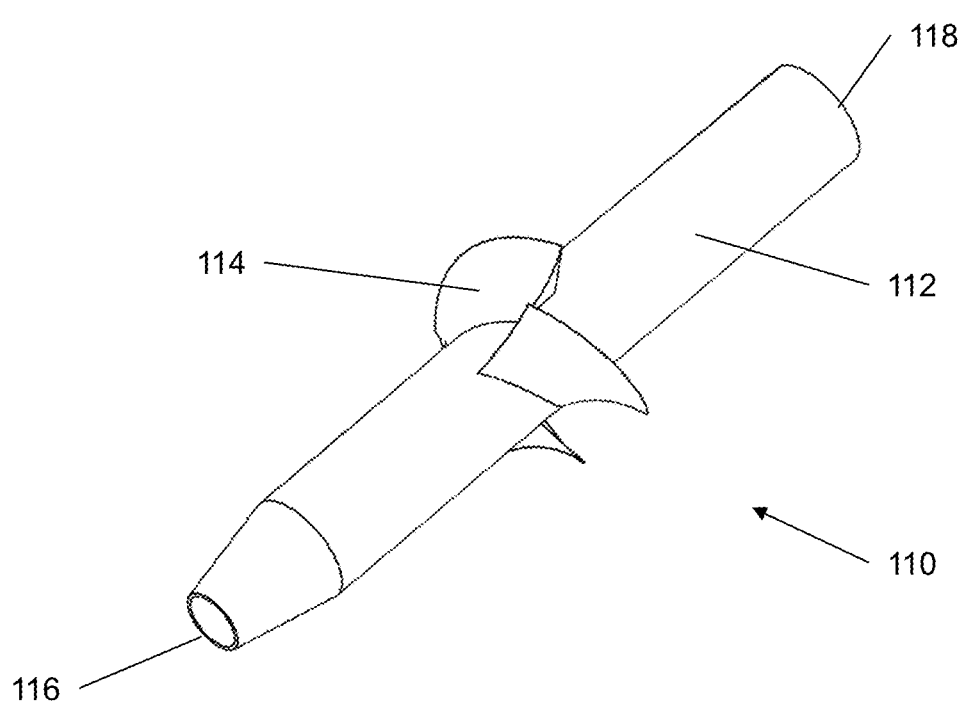
FIG. 1B is a perspective view of one embodiment of a propulsor isolated from the medical implant of FIG. 1A.
Figure 1C:
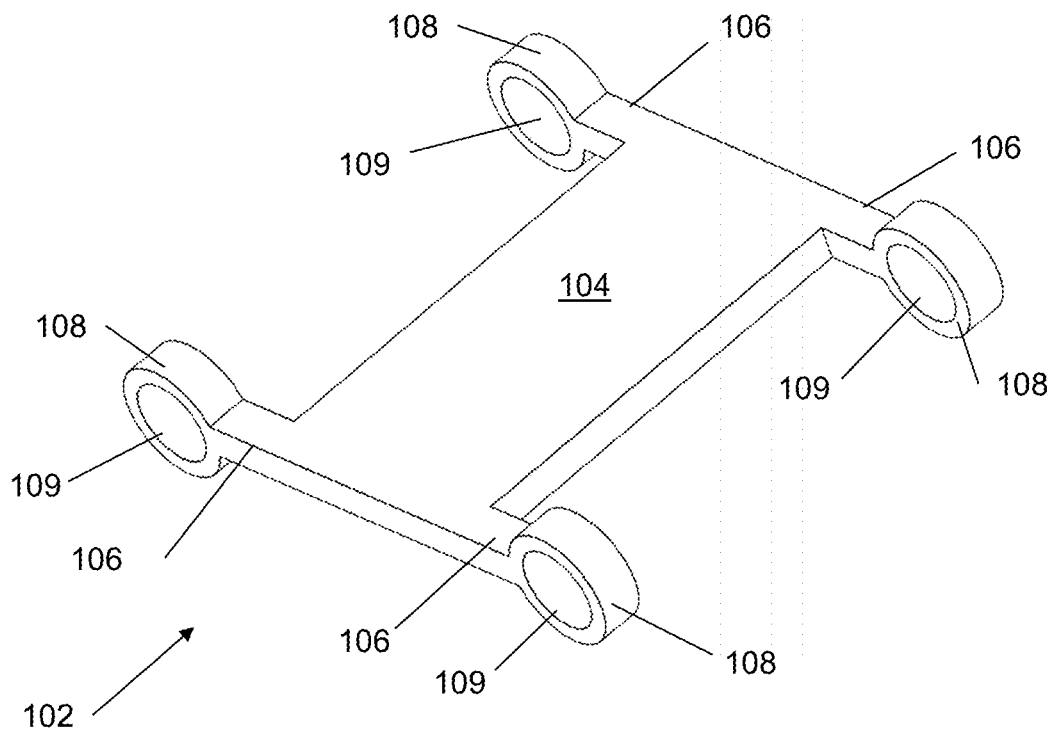
FIG. 1C is a perspective view of one embodiment of a chassis which may be used in the medical implant of FIG. 1A.

Turning now to FIG. 1A, there is a perspective view of one embodiment of a medical implant 100 comprising a chassis 102, a first propulsor 110, and a second propulsor 120. FIG. 1B is a perspective view of one embodiment of the first propulsor 110 isolated from the chassis 102. In certain embodiments, the propulsor 110 comprises a center longitudinal shaft 112 and a propeller 114. In the embodiment illustrated in FIG. 1B, the propeller 114 has a clockwise thread orientation. In contrast, the propeller 124 of the propulsor 120 has a counter-clockwise thread orientation.

In certain embodiments, a distal end 116 of the center shaft 112 may be pointed or have a cutting surface defined therein to allow for easier movement of implant 100 through a medium, such as a boney tissue. In certain embodiments, a proximal end 118 of the center shaft 112 may have torque engagement features (not shown in FIG. 1B) defined therein or upon for engaging with a torque inducing device. For instance, in some embodiments, the torque engagement feature may be a 5 mm hex socket defined within the center shaft for engaging with a 5 mm hex shaped driver of an insertion instrument.

Figure 10:
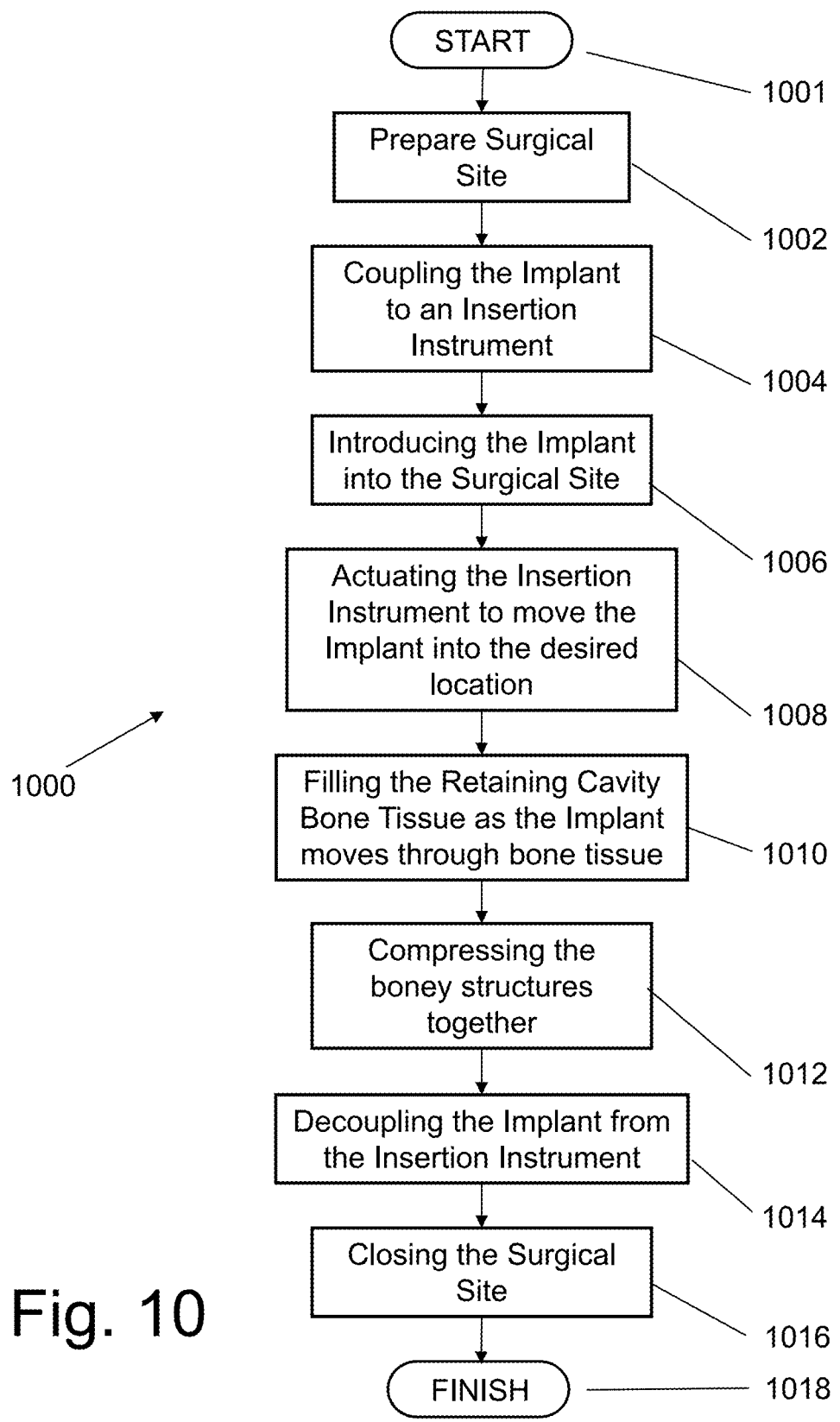
FIG. 10 is a flowchart illustrating a surgical method for inserting and positioning certain embodiments of the implants discussed above.

FIG. 10 is a perspective view of the embodiment of FIG. 1A where the chassis 102 is isolated from both the first propulsor 110 and the second propulsor 120. In the illustrative embodiment, the chassis 102 comprises a center section 104 having a plurality of extension arms 106 extending from the center section 104. In the illustrative embodiment, retaining rings 108 are formed on the outside ends of the extension arms 106. In certain embodiments, retaining rings 108 have generally circular apertures 109 which form generally circular bearing surfaces sized to retain the shafts 112 and 122 of the propulsors 110 and 120, respectively. The circular apertures 109 are sized to allow the shafts 112 and 122 to rotate about their longitudinal axes with respect to the chassis 102 while their inside faces provide a bearing surface for the shafts 112 and 122. The lateral position of the apertures 109 are positioned from the center section 104 of the chassis to allow the propellors 114 and 124 to clear the center section 104 of the chassis 102 so that the propellors can rotate when a torque is applied to the respective propulsor 110 or 120.

Figure 1D:
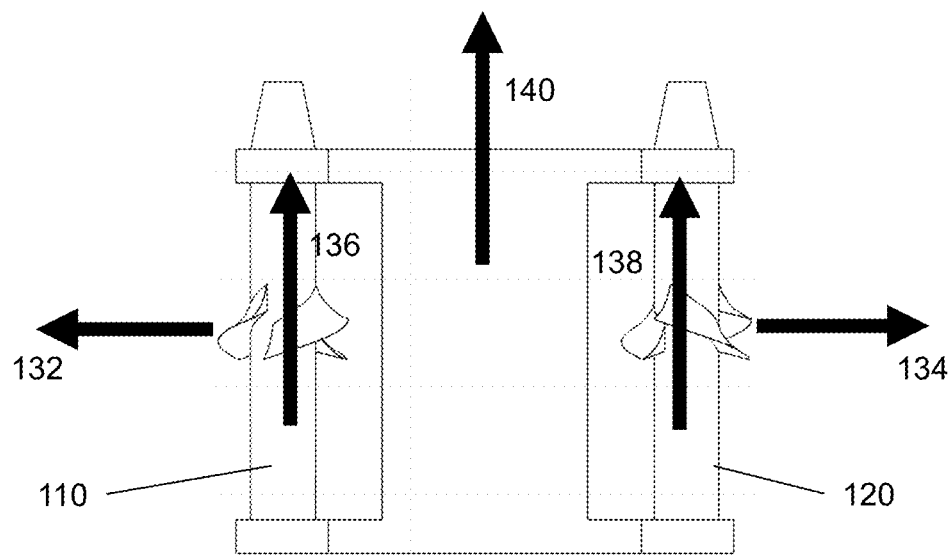
FIG. 1D is a force and directional movement concept diagram of the medical implant of FIG. 1A.

FIG. 1D is a top view of the implant 100 positioned in a medium (not shown), such as boney tissue at a moment when a clockwise rotational force is being applied to the first propulsor 110 while a counter-clockwise rotational force is being applied to the second propulsor 120. The respective rotations cause lateral forces (indicated by arrows 132, 134) and longitudinal forces (indicated by arrows 136, 138) to be applied to the medium, respectively. The lateral forces 132 and 134 are equal in magnitude and opposite in direction. So, they effectively cancel each other. The longitudinal forces 136 and 138, in contrast, are additive in nature and will cause the implant 100 to propel forward within the medium in the direction indicated by the arrow 140. On the other hand, reversing the applied rotational forces or torque will cause the implant 100 to move in a reverse direction with respect to the medium. Thus, by changing the direction of the applied torque to the propulsors 110 and 120, the medical implant 100 can be positioned precisely along a longitudinal insertion path.

Figure 2A:
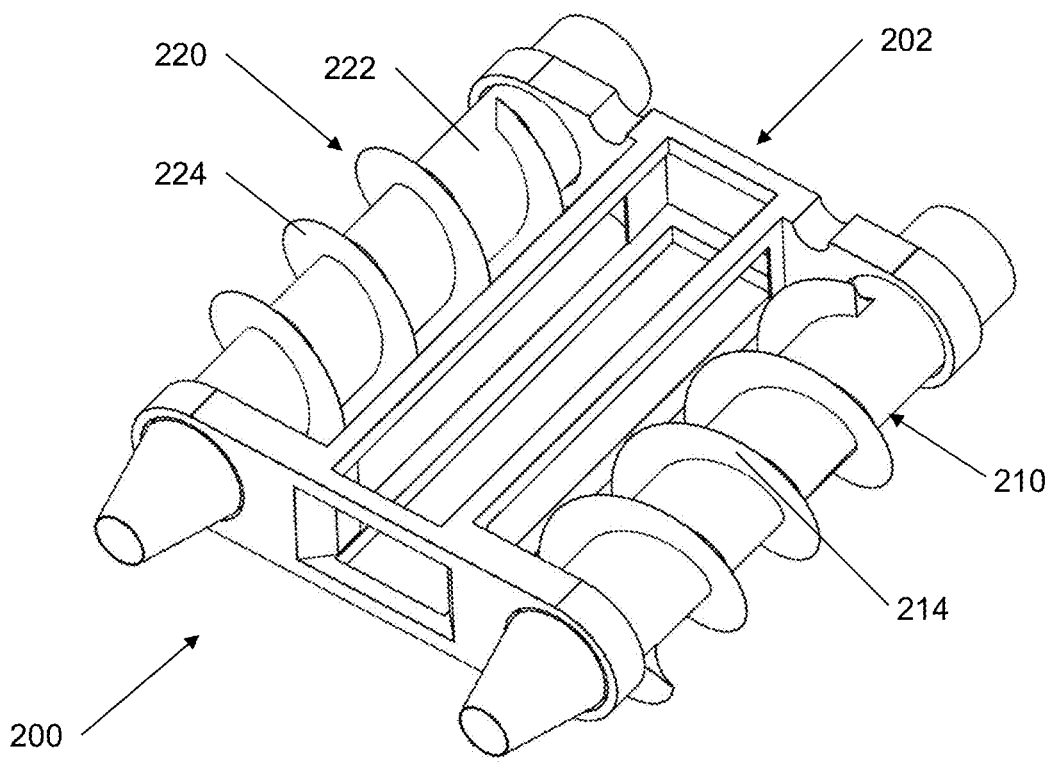
FIG. 2A is a perspective view of another embodiment of a medical implant.
Figure 2B:
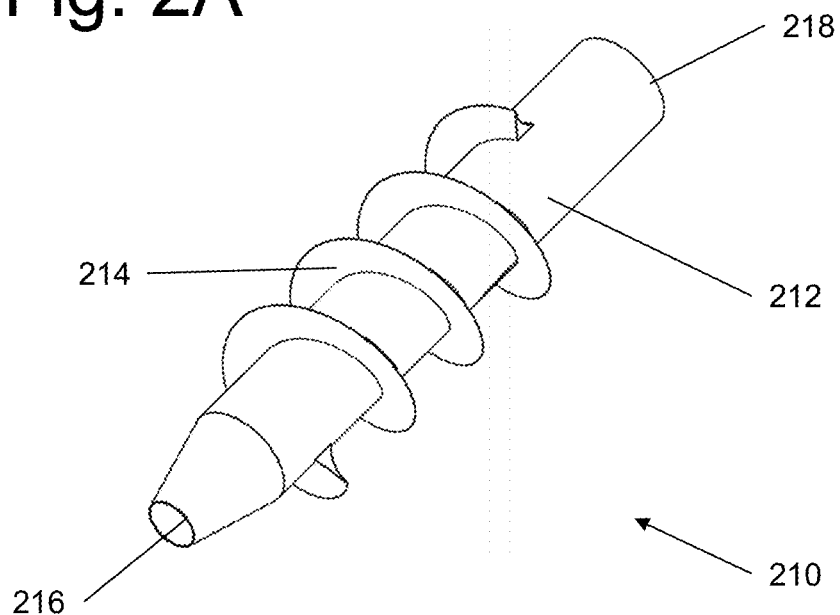
FIG. 2B is a perspective view of a propulsor which may be used with the medical implant of FIG. 2A.

Turning now to FIG. 2A, there is a perspective view of another embodiment of a medical implant 200 comprising a chassis 202, a first propulsor 210, and a second propulsor 220. FIG. 2B is a perspective view of one embodiment of the first propulsor 210 isolated from the chassis 202. In certain embodiments, the propulsor 210 comprises a center shaft 212 and a flight 214. The propulsor 210 is similar to propulsor 110 discussed above except that the propeller 114 has been replaced with an auger thread or flight 214. In certain embodiments, there may be a single flight as illustrated in FIG. 2B. In other embodiments, there may be two, three, or even four flights (not shown) surrounding the center shaft 212. In the embodiment illustrated in FIG. 2B, the flight 214 has a clockwise thread orientation. The flight 224 of the propulsor 220 has a counter-clockwise thread orientation. In contrast to the relatively short length of the propellers 114 and 124 of the embodiment discussed above in reference to FIGS. 1A-1D, flights 214 and 224 are defined along most of the longitudinal lengths of the shafts 212 and 222, respectively.

In certain embodiments, a distal end 216 of the center shaft 212 may be pointed or have a cutting surface defined therein to allow for easier movement of implant 200 through a medium, such as boney tissue. In certain embodiments, a proximal end 218 of the center shaft 212 may have torque engagement features (not shown in FIG. 2B) defined therein or upon for engaging with a torque inducing device. For instance, in some embodiments, the torque engagement feature may be a 5 mm hex socket defined within the proximal end 218 of the center shaft 212 for mating with a 5 mm hex shaped driver of an insertion instrument. In some embodiments, the center shaft may be cannulated to allow for the placement of a guidewire during the implantation process or to inject flowable materials into the cannulation, such as biologics, glues, or other osteogenic or osteororetentive material.

Figure 2C:
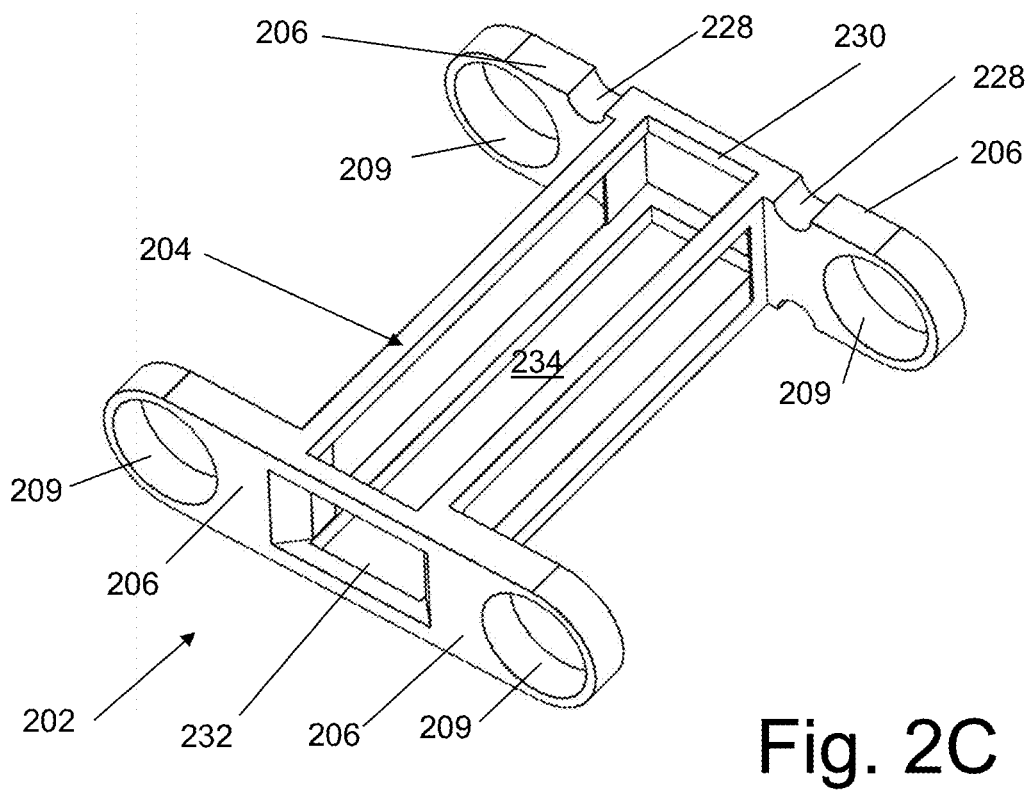
FIG. 2C is a perspective view of a chassis which may be used with the embodiment of FIG. 2A.

FIG. 2C is a perspective view of the embodiment of FIG. 2A where the chassis 202 is isolated from both the first propulsor 210 and the second propulsor 220. In the illustrative embodiment, the chassis 202 comprises a center cage 204 having a plurality of extension arms 206 extending from the center cage 204. Generally circular apertures 209 are defined at the ends of the extension arms 206 to retain the shafts 212 and 222 of the propulsors 210 and 220, respectively. The circular apertures 209 are sized to allow the shafts 212 and 222 to rotate about their longitudinal axes with respect to the chassis 202 while their inside faces provide a bearing surface for the shafts 212 and 222. The lateral position of the apertures 209 from the center cage 204 allow the flights 214 and 224 to clear the center cage so that the flights can rotate when torque is applied to the respective propulsor 210 or 220.

In certain embodiments, bearing surfaces or detents 228 or other such features may be defined in the proximal side 230 of the chassis 202 to allow an insertion instrument to rigidly hold the chassis 202. In yet other embodiments, a propulsor interfacing/retaining feature of the chassis may be comprised of a bearing block, a coupling mechanism, or other common drive transmission coupling feature.

In certain embodiments, the distal end of the chassis 202 has an aperture or open mouth 232 which allows for the harvesting of the bone tissue as the implant 200 moves forward through the boney tissue. In some embodiments, one or more of the members forming the distal end of the chassis may be pointed or sharpened to allow the implant to more easily cut or move through bone tissue as the implant is positioned in the boney tissue. Additionally, one or more cannulations may be formed within the chassis 202 to allow for the placement of a guidewire during the implantation process or to inject flowable materials into the cannulation, such as biologics, glues, or other osteogenic or osteororetentive material. In yet, other embodiments, the chassis 202 may be fenestrated or made from porous materials to allow for bone growth in and around the chassis.

Figure 2D:
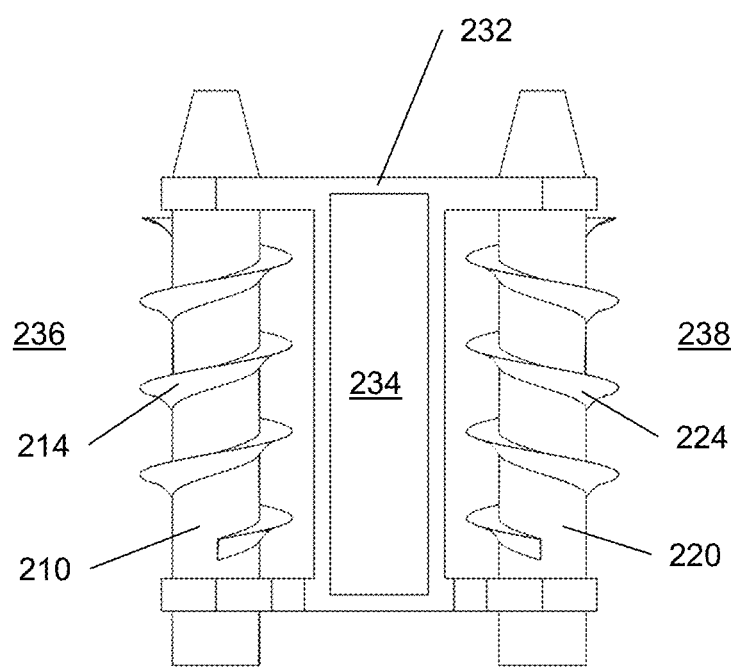
FIG. 2D is a top view of the implant of FIG. 2A.

FIG. 2D is a top view of the implant 200 positioned in a medium (not shown), such as boney tissue, at a moment when a clockwise rotational force is being applied to the first propulsor 210 while a counter-clockwise rotational force is being applied to the second propulsor 220. As explained above in reference to FIG. 1D, such forces will cause the implant 200 to propel forward through the boney tissue. This forward movement tends to push the boney tissue in front of the implant 200 through the aperture or mouth 232 and into a retaining cavity 234. Additionally, the rotation of the flight 214 about the shaft 212 also cuts through the boney tissue on the exterior side 236 of the implant 200. Excess boney tissue from the side 236 is rotated by the flight 214 and into the retaining cavity 234. Similarly, the rotation of the flight 224 about the shaft 222 also cuts through the boney tissue on the exterior side 238 of the implant 200. Excess boney tissue from the side 238 is rotated by the flight 224 and into the retaining cavity 234. Thus, the tissue entering through the mouth 232 and the tissue entering through the sides by the rotation of the flights 214 and 224 "self-fill" the retaining cavity 234 local tissue graft material and compresses that same harvested material within the retaining cavity as the implant is propelled forward. Such self-grafting within the implant 200 may encourage bridging boney fusion.

As the medical implant 200 advances further along its intended insertion path, additional boney tissue is harvested into the retaining chamber as explained above. The additional harvesting or filling of the retaining cavity 234 may cause a compaction of the boney tissue inside of the retaining cavity.

Figure 3A:
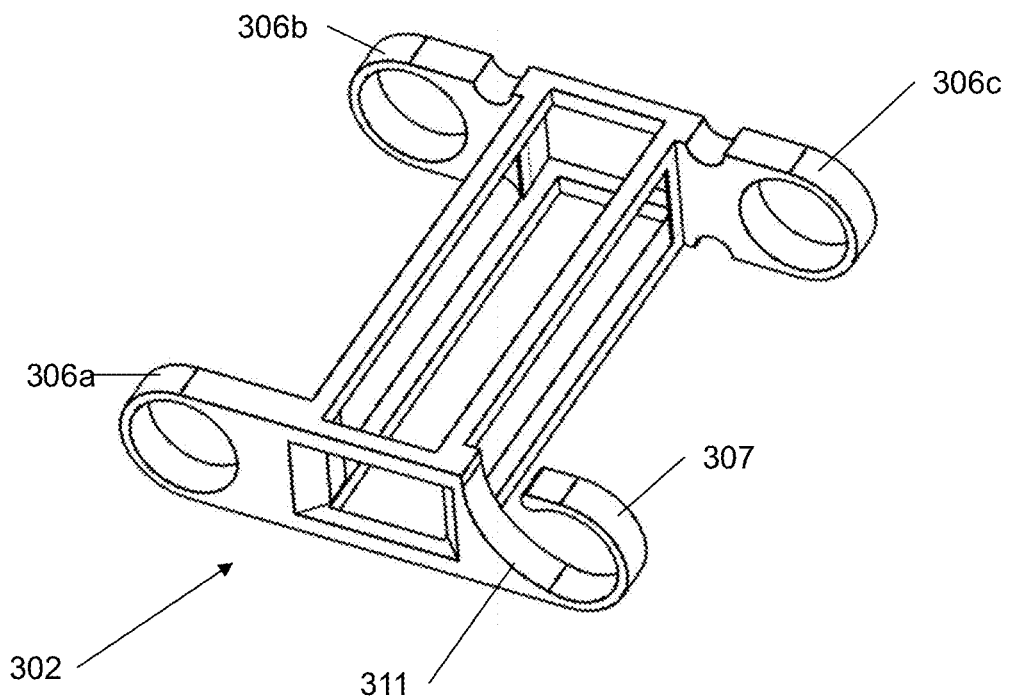
FIG. 3A is a perspective view of an alternative embodiment of a chassis which may be used in various embodiments of the present invention.
Figure 3B:
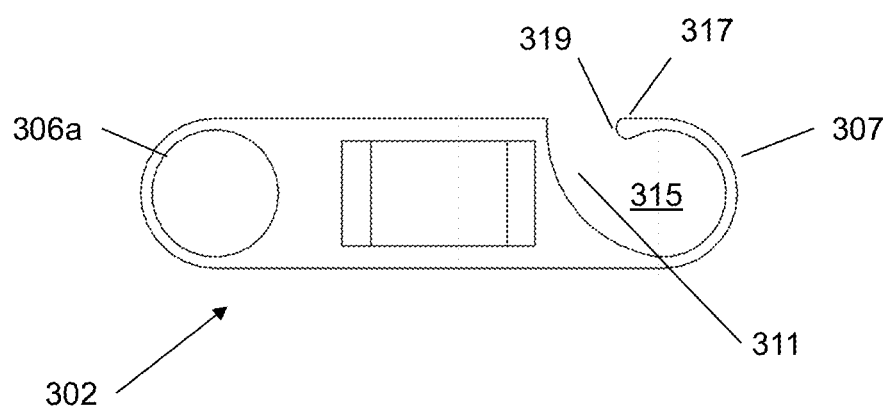
FIG. 3B is a partial front view of the chassis of FIG. 3A illustrating the distal end.

FIG. 3A is a perspective view of an alternative embodiment of a chassis 302 which may be used in various embodiments of the present invention. FIG. 3B is a partial front view of the chassis 302 illustrating the distal end. Chassis 302 is similar to the chassis 202 except one or more of the distal extension arms may be modified to allow for easier placement of the propulsors within the apertures of the extension arms. For brevity and clarity, a description of those parts which are identical or similar to those described in connection with chassis 202 will not be repeated here. Reference should be made to the foregoing paragraphs with the following description to arrive at a complete understanding of chassis 302. As illustrated in FIGS. 3A and 3B, the chassis 302 has three extension arms 306a-306c which are similar to extension arms 206 discussed above. However, the chassis 302 has a modified extension arm 307 which has a channel 311 defined therein from an exterior face of the arm to an interior aperture or retaining space 315. The channel 311 may be narrower towards the exterior face and larger towards the retaining space 315. In certain embodiments, an edge clip 317 may be formed in the wall of the extension arm 307 adjacent to the channel 311. In certain embodiments, the edge clip may have a rounded edge 319.

When assembling an implant, a proximal end of a propulsor, such as propulsor 210 (not shown) may be inserted into the aperture 306c. A portion of the distal end of the propulsor may be then be inserted into the channel 311 and pushed past the edge clip 317 until it is fully seated within the retaining space 315. The edge clip 317 and the tapering of the channel 311 then prevents the propulsor from backing out of the channel 311. Although FIGS. 3A and 3B only shows one modified extension arm 307 with a channel 311, one skilled in the art would recognize that additional channels and edge clips may be defined in any one of the extension arms 306a through 306c. For instance, in certain embodiments, extension arm 306a may be modified to become a mirror image of extension arm 307.

Figure 4A:
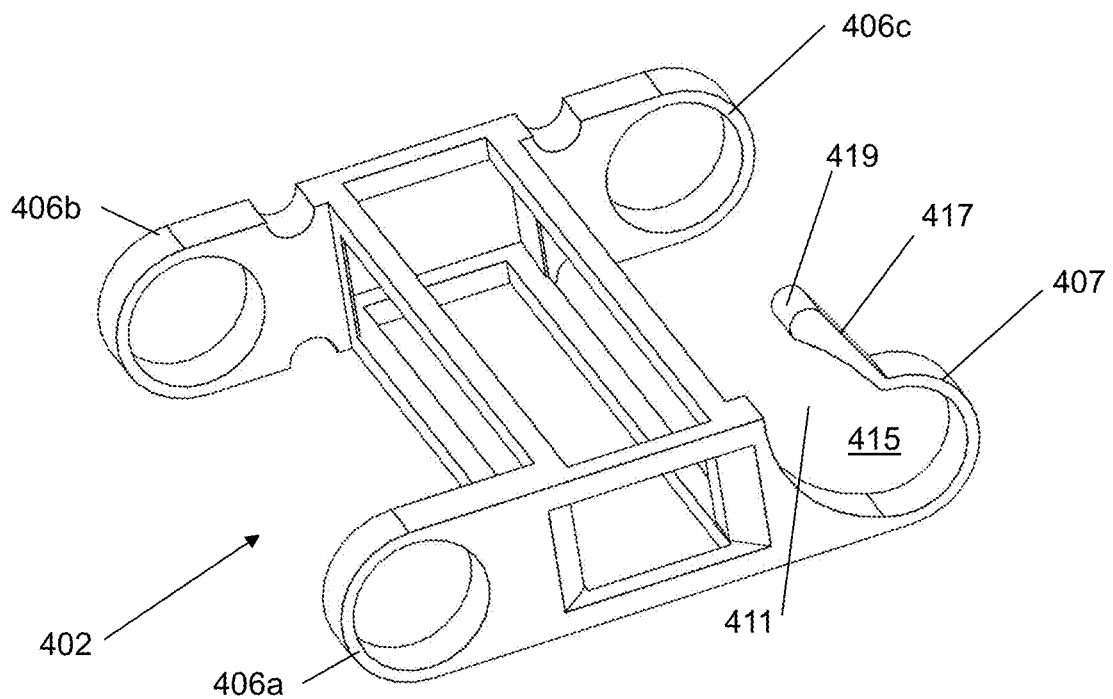
FIG. 4A illustrates an alternative embodiment of a chassis of a medical implant with an extension arm in an open position or configuration.
Figure 4B:
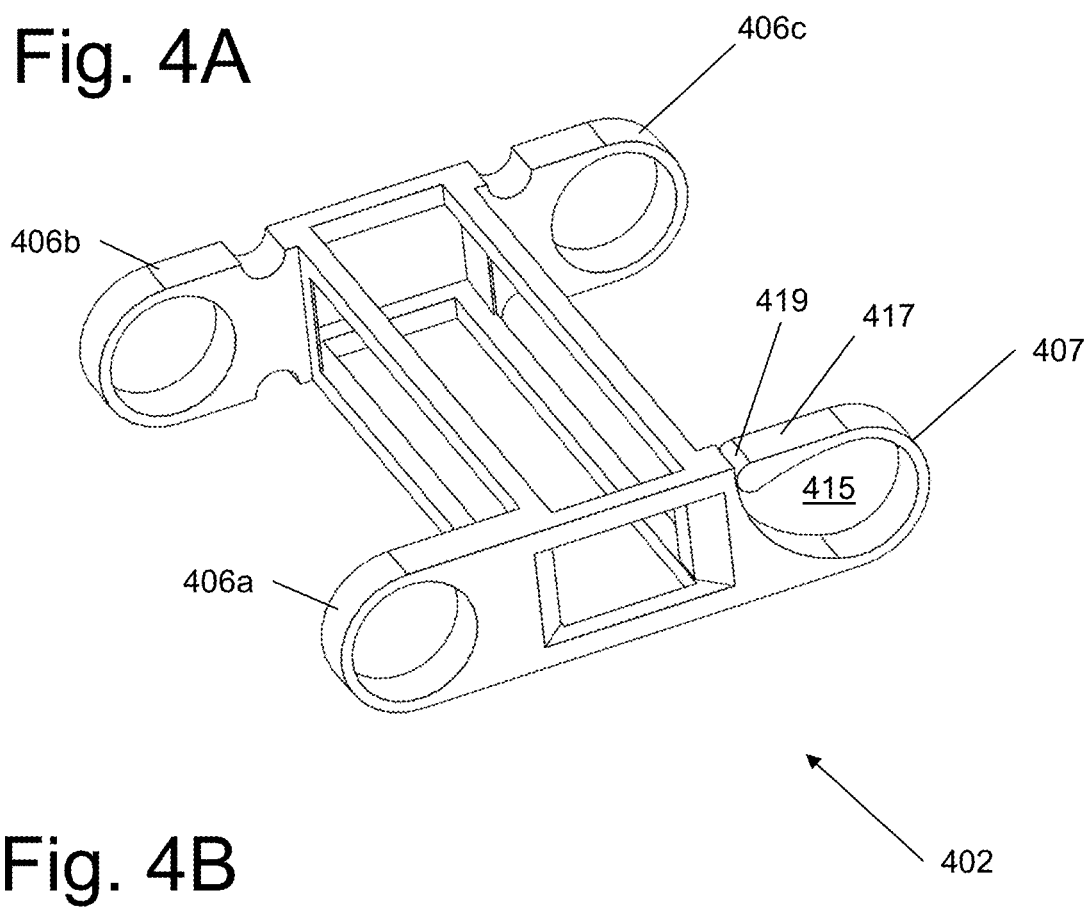
FIG. 4B illustrates the medical implant of FIG. 4A with the extension arm in a closed position or configuration.

FIGS. 4A and 4B are perspective views of an alternative embodiment of a chassis 402 which may be used in various embodiments of the present invention. Chassis 402 is similar to the chasses 202 and 302 described above except one or more of the distal extension arms may be modified to allow for easier placement of the propulsors (not shown) within the apertures of the extension arms. For brevity and clarity, a description of those parts which are identical or similar to those described in connection with chasses 202 and 302 will not be repeated here. Reference should be made to the foregoing paragraphs with the following description to arrive at a complete understanding of chassis 402.

FIG. 4A illustrates the chassis 402 with a modified extension arm 407 in an open position or configuration. In contrast, FIG. 4B illustrates the extension arm 407 in a closed position or configuration. In certain embodiments, the extension arm 407 has a retaining clip 417 sized to allow passage of a portion of a propulsor (not shown) through an opening 411 when the retaining clip 417 is open as illustrated in FIG. 4A. In certain embodiments, the retaining clip 417 may have an edge 419 designed to mate with a retaining feature, such as an indent (not shown) formed on an opposing surface of the chassis 402.

When assembling an implant, a proximal end of a propulsor, such as propulsor 210 (not shown) may be inserted into the aperture 406c. When the retaining clip 417 is in an open configuration such as illustrated in FIG. 4A, a portion of the distal end of the propulsor may be inserted into the opening 411 and into the retaining space 415. The retaining clip 417 may then be closed as illustrated in FIG. 4B which prevents the propulsor from backing out of the opening 411. Although FIGS. 4A and 4B only shows one modified extension arm 407 with an opening 411 and retaining clip 417, one skilled in the art would recognize that additional openings and clips may be defined in any one of the extension arms 406a through 406c. For instance, extension arm 406a may be modified to become a mirror image of extension arm 407.

Figure 5A:
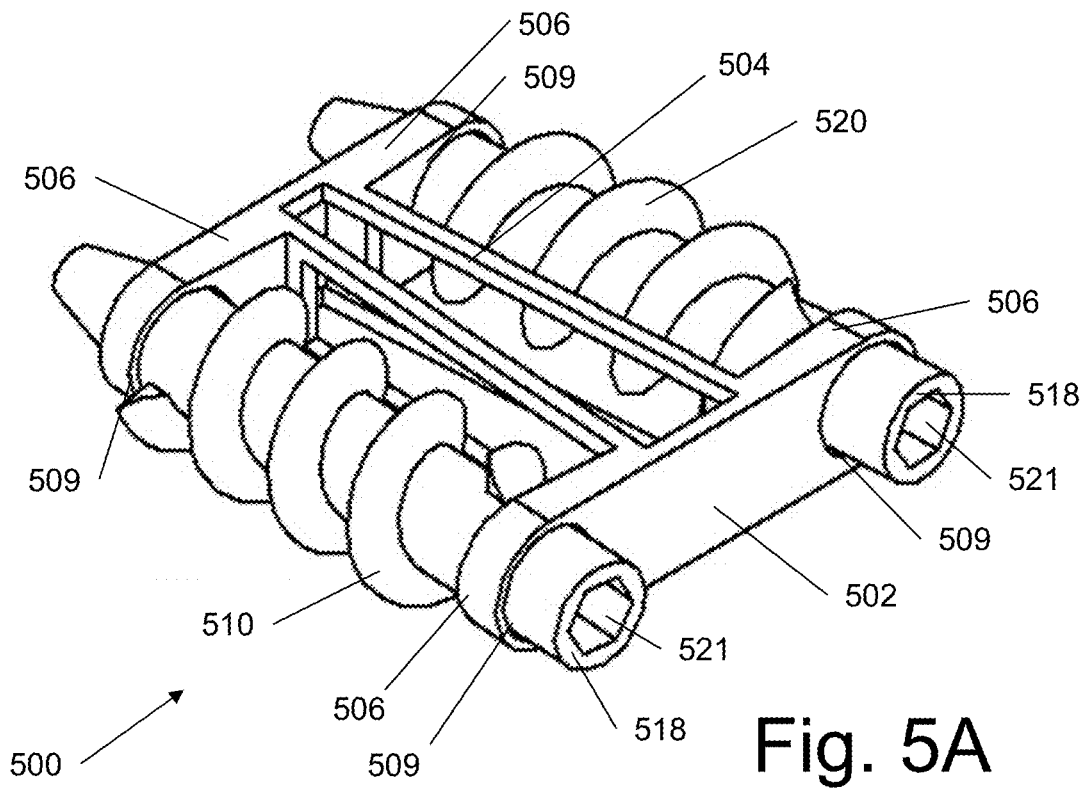
FIG. 5A is a perspective view of another embodiment of a medical implant illustrating a proximal end of the implant.

Turning now to FIG. 5A, there is a perspective view of another embodiment of a medical implant 500 illustrating a proximal end of the implant. The implant 500 comprises a chassis 502, a first propulsor 510, and a second propulsor 520. Chassis 502 is similar to the chassis 202 described above except the center cage 504 of the chassis 502 tapers inwardly from the proximal end to the distal end. For brevity and clarity, a description of those parts which are identical or similar to those described in connection with chassis 202 will not be repeated here. Reference should be made to the foregoing paragraphs with the following description to arrive at a complete understanding of implant 500. As illustrated in FIG. 5A, the width of the center cage 504 at the proximal end is greater than the width of the center cage at the distal end and the length of extension arms 506 remain generally the same length. Thus, when the first propulsor 510 and the second propulsor 520 are positioned within the respective apertures 509, the propulsors angle toward each other and their longitudinal axes converge or intersect at a point forward to the implant. In certain embodiments, the apertures 509 are also angled with respect to the longitudinal axis of the implant 500 so that the respective bearing surfaces are generally parallel with the longitudinal axes of each respective propulsor 510 and 520. In yet other embodiments, the propulsors angle away from each other and their longitudinal axes converge or intersect at a point behind the implant.

Note that in FIG. 5A, the proximal ends 518 of the propulsors show torque engagement features 521 defined therein or upon for engaging with a torque inducing device. As discussed above in reference to FIG. 2B, the torque engagement feature 521 in this exemplary embodiment may be a 5 mm hex socket defined within the proximal ends 518 for mating with a 5 mm hex shaped driver of an insertion instrument (not shown).

Figure 5B:
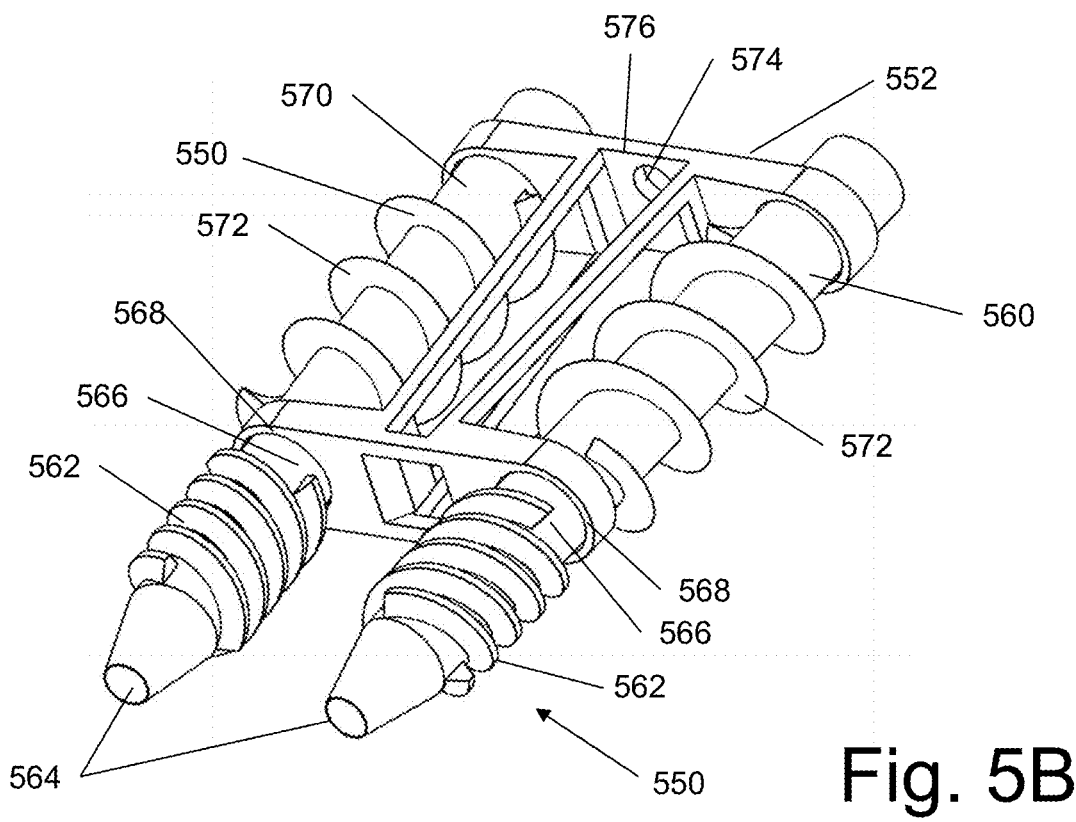
FIG. 5B is a perspective view of another embodiment of a medical implant.

FIG. 5B is a perspective view of another embodiment of a medical implant 550. The implant 550 comprises a chassis 552, a first propulsor 560, and a second propulsor 570. The implant 550 is similar to the implant 500 described above except the implant 550 includes different embodiments for the propulsors. For brevity and clarity, a description of those parts which are identical or similar to those described in connection with above chasses will not be repeated here. Reference should be made to the foregoing paragraphs with the following description to arrive at a complete understanding of the medical implant 550.

In the illustrative embodiment of FIG. 5B, each of the propulsors 560 and 570 include an additional threaded region 562 which is between its distal end 564 and a smooth bearing surface 566 which is enclosed by an aperture 568 of the distal extension arm of the chassis 552. In certain embodiments, this additional threaded region 562 provides the requisite interaction with boney tissue to propel the implant 550 forward until the flight 572 can interact with the boney tissue as described above in reference to other embodiments.

FIG. 5B also illustrates an alternative proximal aperture 574 defined in the proximal side 576 of the chassis 552. In certain embodiments, the proximal aperture 574 allows for supplemental fixation, such as a screw or nail (not shown) to anchor the implant 550 in place after positioning.

Figure 6A:
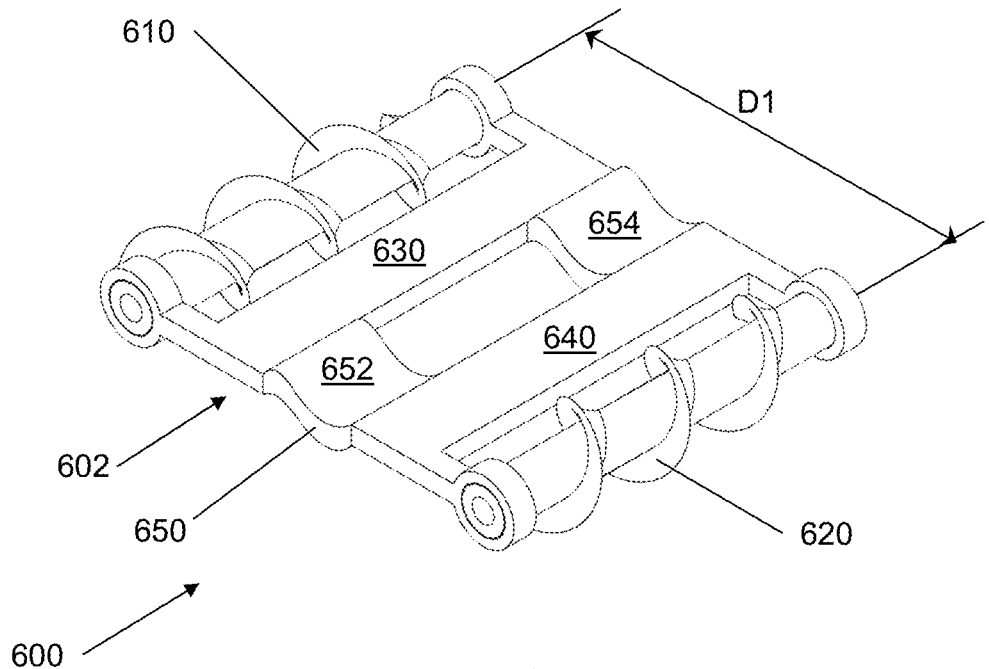
FIG. 6A is a perspective view of an alternative embodiment of a medical implant in a first or relaxed configuration.
Figure 6B:
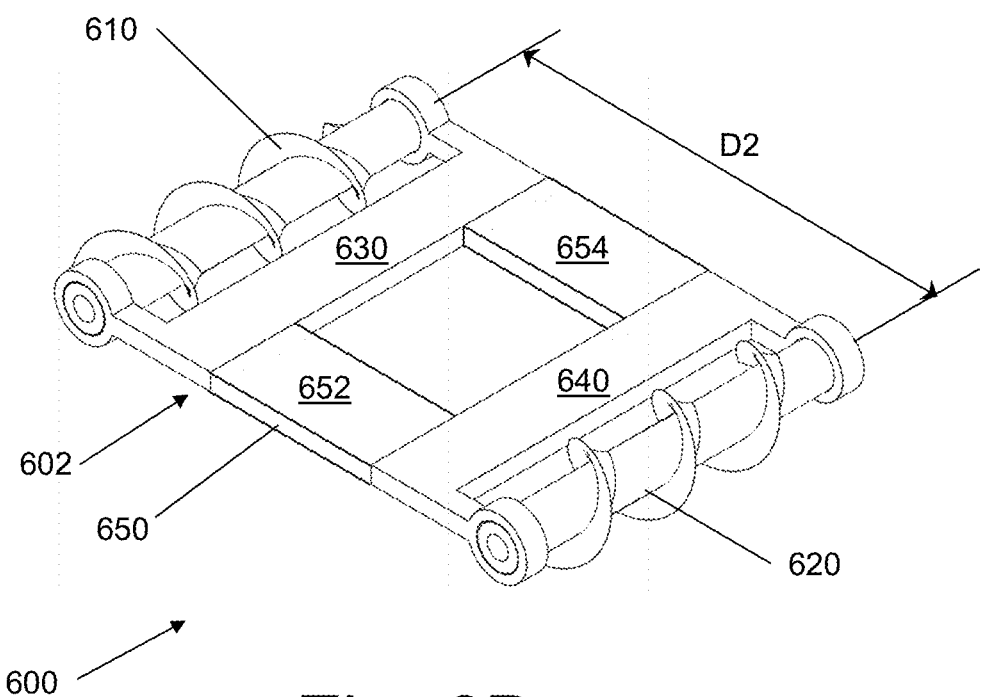
FIG. 6B is an isometric view of the medical implant of FIG. 6A in a second or tensioned configuration.

FIG. 6A is a perspective view of an alternative embodiment of a medical implant 600 in a first or relaxed configuration. FIG. 6B is an isometric view of the medical implant 600 in a second or tensioned configuration. The medical implant 600 is similar to the implants described above except that the center chassis has a flexible region which allows the chassis to be "pre-tensioned" or biased prior to insertion and positioning. For brevity and clarity, a description of those parts which are identical or similar to those described above will not be repeated here. Reference should be made to the foregoing paragraphs with the following description to arrive at a complete understanding of the implant 600.

In the illustrative embodiment, the implant 600 comprises a chassis 602, a first propulsor 610, and a second propulsor 620. In certain embodiments, the chassis 602 comprises a first outside ridged portion 630 and a second outside ridged portion 640. A flexible interior region or portion 650 couples the first ridged portion 630 to the second ridged portion 640. In the illustrative embodiment, the flexible interior portion comprises a first or distal flexible member 652 and a second or proximal flexible member 654. In other embodiments, there may be a single flexible member (not shown). In certain embodiments, the flexible members may comprise an elastomeric material, such as Ethylene Propylene Diene Monomer ("EPDM"), Perfluoroelastomer (FFKM), Fluoroelastomer (FKM), or Nitrile.

In FIG. 6A, both the distal and proximal flexible members are in a first or "relaxed" configuration such that the first propulsor 610 and the second propulsor 620 are spaced at a distance D1 from each other. In FIG. 6B, both the distal and proximal flexible members are in a second or "tensioned" configuration such that the first propulsor 610 and second propulsor 620 are spaced at a distance D2 from each other. As illustrated, length D2 is greater than the length D1 which causes the flexible members to be stretched or biased. Such stretching or biasing can occur when the implant 600 is positioned onto an inserter and or when guide holes are drilled into the boney material at a length D2 from each other. Once the flexible members are stretched or pre-tensioned so that the propulsors are at a distance D2 from each other, the implant 600 may be inserted and positioned into the boney tissue and the inserter removed. Such pre-tensioning or biasing will cause the two boney structures to actively compress against each other as the flexible members attempt to return to a first or relaxed configuration.

In other embodiments, the flexible interior portion may form a mechanical linkage (such as a scissor linkage), which after implantation, may be mechanically actuated to expand or compress the surrounding boney tissue.

In yet other embodiments, the flexible interior portion 650 may be made from nickel titanium (also known as Nitinol®) or another shape memory alloy. The flexible portion 650 would have a specific shape (i.e., a straight or linear shape) at a cooler temperature, such as room temperature. Once inserted into a human body, the metal would rise to a body temperature which will cause the anchor to change shape (i.e., to change from a linear shape to a curve shape) to enhance compression.

Figure 7:
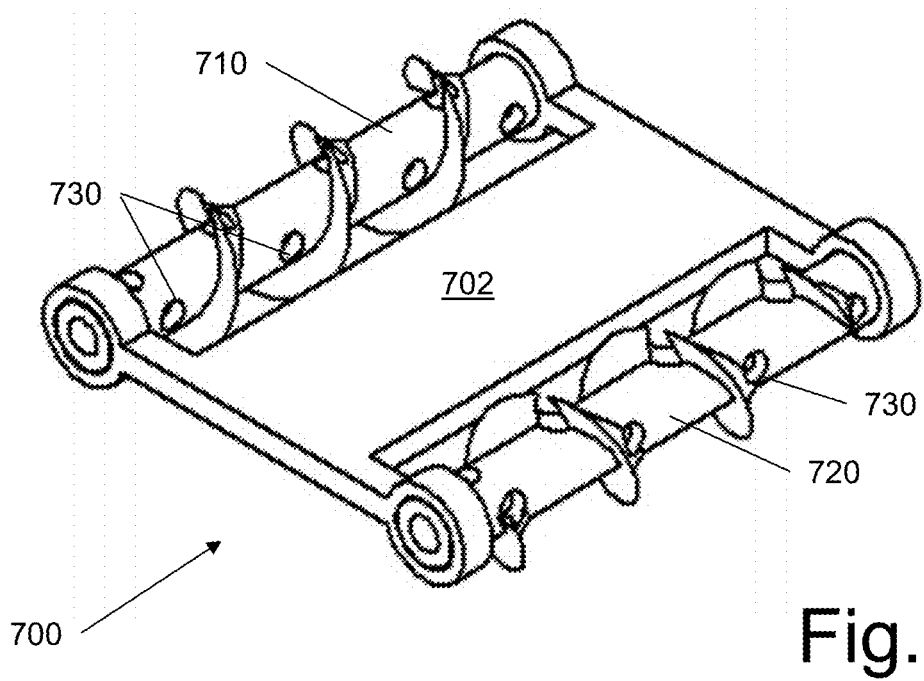
FIG. 7 is a perspective view of another embodiment of a medical implant.

Turning now to FIG. 7, there is a perspective view of another embodiment of a medical implant 700 illustrating a proximal end of the implant. The implant 700 comprises a chassis 702, a first propulsor 710, and a second propulsor 720. Chassis 702 is similar to the chassis 102 described above. In this illustrated embodiment, the first and second propulsors 710 and 720 are fenestrated with a plurality of apertures 730 to encourage bone growth through the propulsors after positioning and placement. For brevity and clarity, a description of those parts which are identical or similar to those described in connection with the implants discussed above will not be repeated here. Reference should be made to the foregoing paragraphs with the following description to arrive at a complete understanding of the implant 700. Such an implant 700 may be suited for small boney interfaces where a larger center cage would be obtrusive to the surgical outcome.

Figure 8:
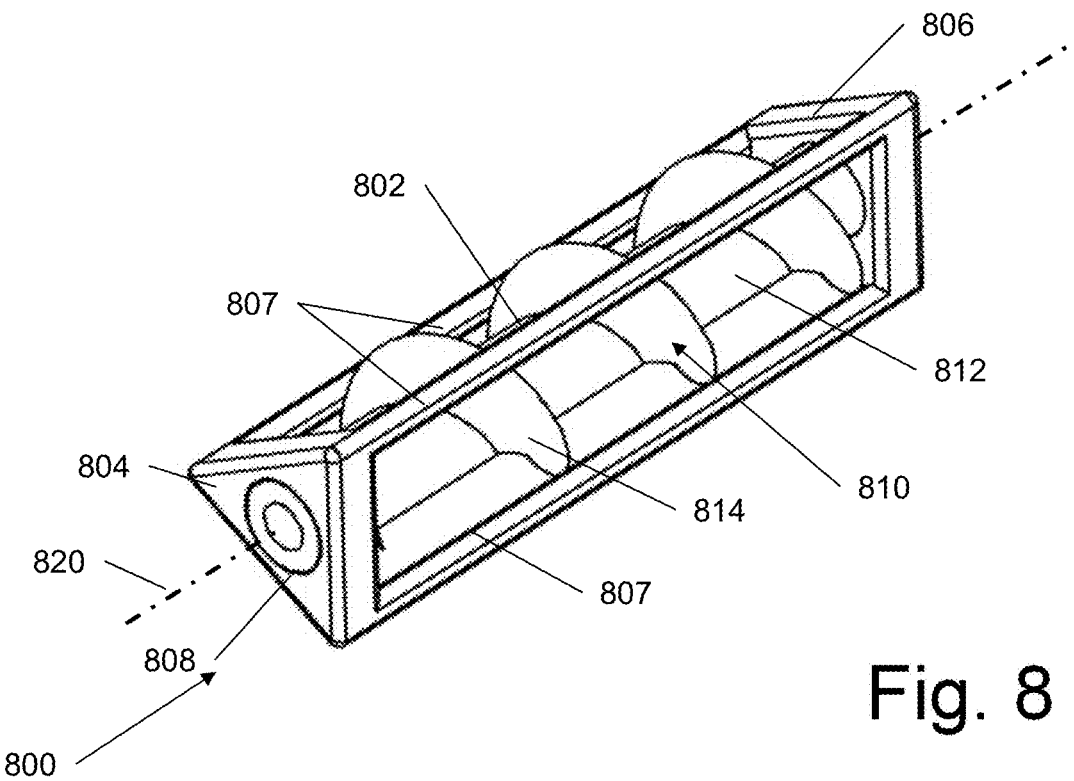
FIG. 8 is an isometric view of an alternative embodiment of a medical implant having a single propulsor.

FIG. 8 is an isometric view of an alternative embodiment of a medical implant 800. The implant 800 comprises a longitudinal chassis or cage 802 and a single propulsor 810 centered on the longitudinal axis 820 of the chassis 802. For brevity and clarity, a description of those parts which are identical or similar to those described in connection with the implants discussed above will not be repeated here. Reference should be made to the foregoing paragraphs with the following description to arrive at a complete understanding of the implant 800.

The exemplary cage 802 comprises a distal triangular plate 804 and a proximal triangular plate 806. The distal triangular plate 804 defines a center aperture 808 sized to allow a center shaft 812 of the propulsor 810 to rotate about the longitudinal axis 820. Similarly, the proximal triangular plate 806 defines a center aperture (not shown) which is also sized to allow the center shaft 812 of the propulsor 810 to rotate about the center axis 820.

In the illustrative embodiment, there are three longitudinal legs 807 joining the distal triangular plate 804 to the proximal triangular plate 806. The lateral distance of the legs 807 from the longitudinal axis 820 are spaced such that the legs clear a rotating flight 814 of the propulsor 810, but are close enough to still allow an interaction between the flight 814 and the surrounding boney tissue (not shown) so that rotating the flight 814 of the propulsor 810 propels and positions the entire implant 800 as described above with respect to other embodiments.

In certain embodiments the implants (such as implant 200) may be manufactured utilizing 3D printing where the implant is printed as a relatively complete assembly incorporating the propulsors 210, 220 and various versions of the chassis. Such embodiments may then be finalized with standard machining methods to clean-up or add various surfaces and features. In yet other embodiments, the chassis or propulsors, may be separated into multiple pieces so that they may be assembled to form a complete implant. The assembled component pieces may then be joined by manufacturing methods, such as but not limited to pinning, gluing, welding, crimping, or snap-fit.

In other embodiments, the chasses may be cannulated to allow the implant to be guided using a surgical guide wire during the implantation process or to inject flowable materials into the cannulation, such as biologics, glues, or other osteogenic or osteroretentive material. In yet, other embodiments, the chassis of the various embodiments may be fenestrated or made from porous materials to allow for bone growth in and around the chassis.

In certain embodiments, the implants and propulsors discussed above may be fabricated from any number of biocompatible implantable materials, including but not limited to Titanium Alloys (Ti 6Al4V ELI, for example), commercially pure titanium, Chromium Cobalt (Cr—Co) and/or stainless steels. In yet other embodiments, the implants and propulsors may also be manufactured from polymer, including Carbon Fiber Reinforced Polymer ("CFRP") with a high carbon mass percentage. In some embodiments, the implants (or portions of the implants) may be coated with a bone conducting surface treatment to increase the potential of bone on-, through-, or in-growth.

In certain embodiments, aspects of the invention may include a surgical kit comprising multiple implants of different size ranges.

One skilled in the art would recognize that individual features discussed in connection with certain exemplary chasses and propulsors described above may be combined with the features of other chasses and propulsors. Such combinations are still within the inventive concept described herein.

Insertion Instrument

Figure 9A:
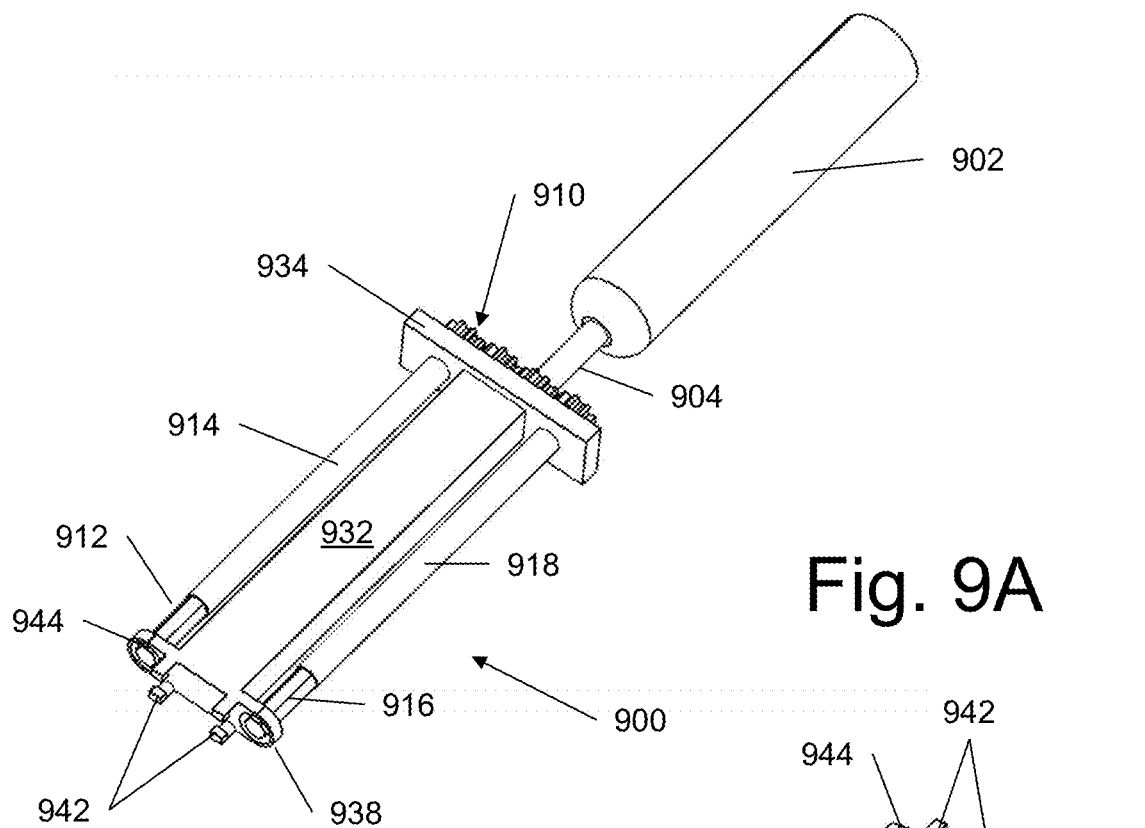
FIG. 9A is a perspective view of an assembled insertion instrument from a distal perspective.
Figure 9B:
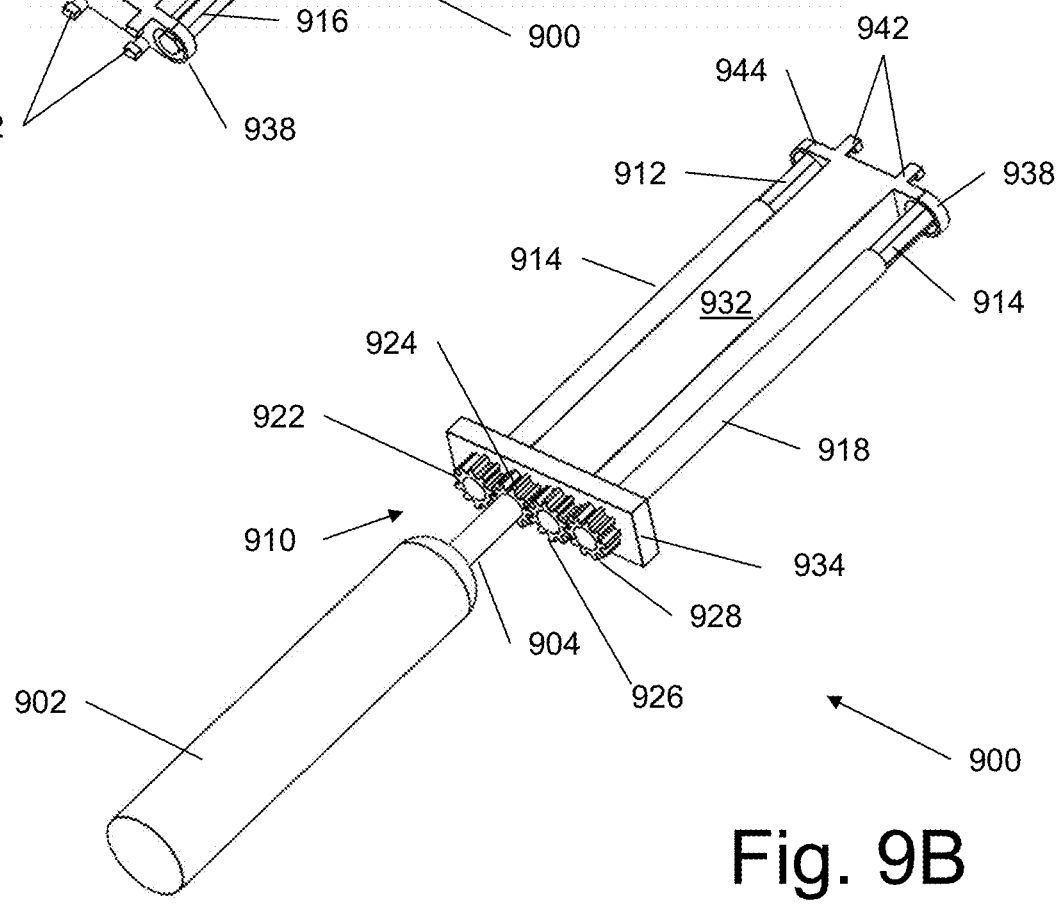
FIG. 9B is a perspective view of the assembled insertion instrument of FIG. 9A from a proximal perspective.
Figure 9D:
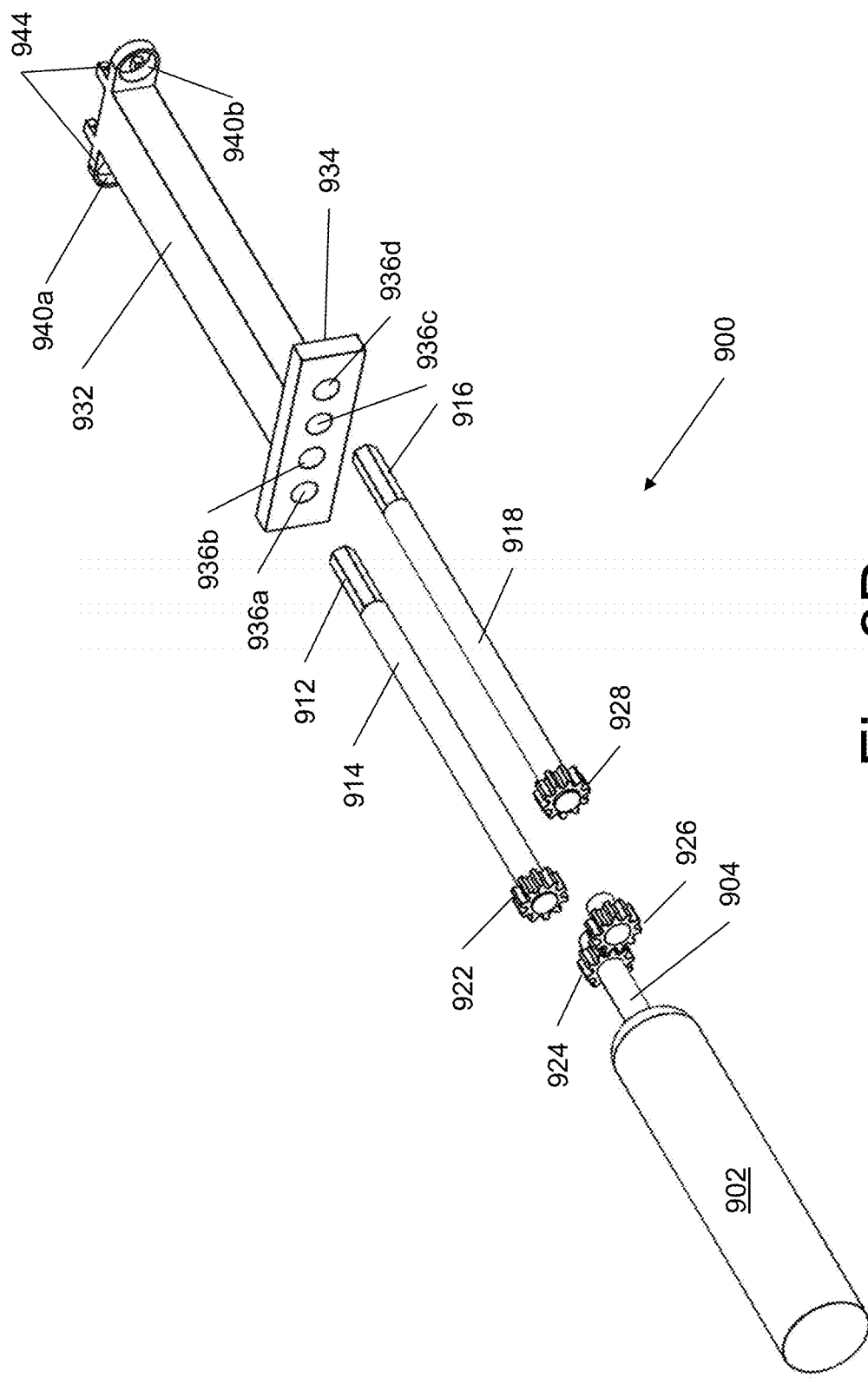
FIG. 9D is a perspective view of the exploded insertion instrument of FIG. 9A from a proximal perspective.

FIG. 9A is a perspective view of an assembled insertion instrument 900 from a distal perspective. FIG. 9B is a perspective view of the assembled insertion instrument 900 from a proximal perspective. FIG. 9C is a perspective view of the exploded insertion instrument 900 from a distal perspective. FIG. 9D is a perspective view of the exploded insertion instrument 900 from a proximal perspective.

In certain embodiments, a handle 902 or another torque inducing mechanism is positioned at the proximal end of the insertion instrument 900. The handle 902 is fixedly coupled to a proximal end of a longitudinal primary or actuating shaft 904. In certain embodiments, the actuating shaft 904 is coupled to a drive train 910 which: (1) transmits the torque and/or rotation from the actuating shaft to induce torque and/or rotation in a first rotational direction to a first secondary shaft 914, and (2) to induce torque and/or rotation in an opposite rotational direction to a second secondary shaft 918. In certain embodiments, distal ends 912 and 916 of the first and second secondary shafts ends are shaped to mate with a torque engagement feature of the propulsors of an implant as described above. For instance, in the illustrative embodiment, the distal ends 912 and 916 of the secondary shafts 914 and 918 are sized and shaped to mate with a 5 mm hex socket defined within the proximal ends of the propulsors as described above.

In certain embodiments, the drive train 910 comprises a four in-line spur gears 922, 924, 926 and 928 aligned in a lateral direction as best illustrated in FIG. 9B. In the illustrative embodiment, spur gear 924 is fixedly coupled to the actuating shaft 904, spur gear 922 is fixedly coupled to the first secondary shaft 914, spur gear 926 is fixedly coupled to an idler shaft 930 (see FIG. 9C), and spur gear 928 is fixedly coupled to the second secondary shaft 918. In other embodiments, the drive train 910 may be composed of belts, drive shafts, chain, and/or shaft couplers.

A mounting unit 932 comprises an alignment plate 934 at its proximal end which couples to and interacts with the shafts 904, 914, 918, and 930. In the illustrative embodiment, four alignment apertures 936a-936d are defined within the alignment plate 934 as best illustrated in FIG. 9D. The four alignment apertures 936a-936d laterally align: the actuating shaft 904, the first secondary shaft 914, the second secondary shaft 918, and the idler shaft 938. In certain embodiments, retaining rings and corresponding indents within the alignment apertures 936a-936d retain and keep the shafts longitudinally positioned but allow the shafts to rotate with respect to the alignment plate 934.

At the distal end of the mounting unit 932, there are two retaining arms 944 extending in a lateral direction from the main body of the mounting unit 932. In certain embodiments, two supporting apertures 940a and 940b are defined within the retaining arms 944 as best illustrated in FIGS. 9C and 9D. When the insertion tool is assembled, the first secondary shaft 914 extends through alignment aperture 936d and through the supporting aperture 940b and can rotate freely with respect to both apertures. Similarly, the second secondary shaft 918 extends through alignment aperture 936a and through the supporting aperture 940a and can rotate freely with respect to both of these apertures.

In certain embodiments, there may be a plurality of retaining features, such as a plurality of fingers 942 which correspond to bearing surfaces or detents defined in the proximal side of the chassis of the medical implants to allow the insertion instrument 900 to rigidly hold the medical implants described above.

In certain embodiments, the handle 902 is designed to impart a torque or rotation on the actuating shaft 904 when a user turns the handle 902. If necessary, the user may also hold the mounting unit 932 or the alignment plate 934 to provide stability and counter-torque when the handle 902 is turned during insertion and deployment of the implants. As the actuating shaft 904 rotates, for instance in a clockwise direction, the spur gear 924 will also rotate in a clockwise direction. The clockwise rotation of spur gear 924 will cause a counter clockwise rotation of spur gear 922 which will cause the counter clockwise rotation of the first secondary shaft 914. Additionally, the clockwise rotation of the spur gear 924 will also cause a counter-clockwise rotation of spur gear 926 which, in turn, causes the clockwise rotation of spur gear 928. Because spur gear 928 is rigidly coupled to the second secondary shaft 918, the clockwise rotation of the spur gear 928 will cause the rotation of the second secondary shaft 918. Thus, as the handle 902 is rotated in a clockwise direction, the first secondary shaft 914 rotates in a counter-clockwise rotation and the second secondary shaft 918 rotates in a clockwise rotation.

Operation and Method of Use

Figure 11A:
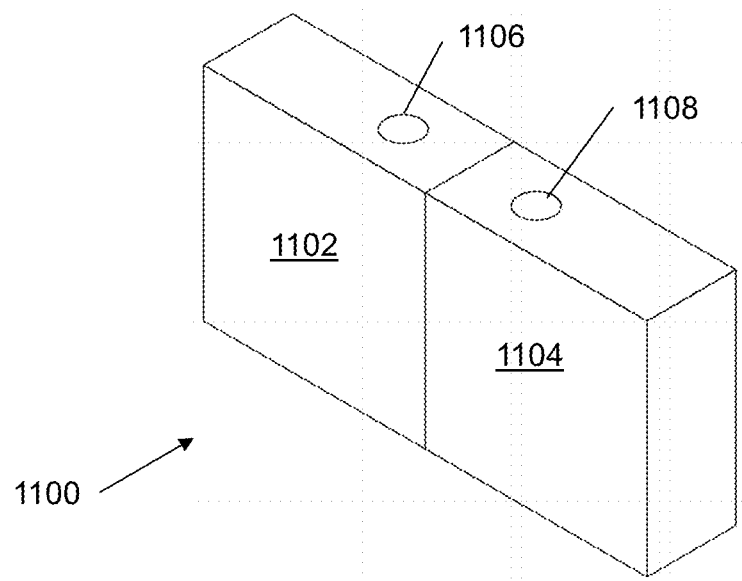
FIG. 11A is a conceptual perspective illustration depicting a surgical site.
Figure 11B:
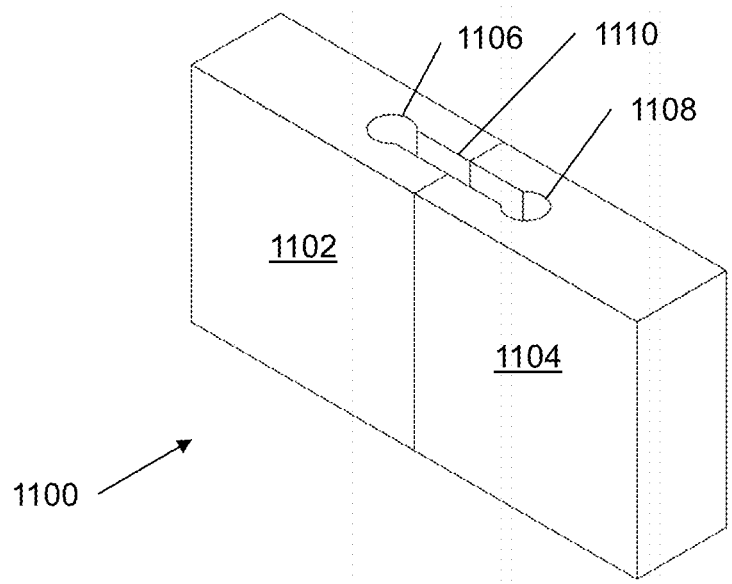
FIG. 11B is a conceptual perspective illustration of an alternative surgical site.
Figure 12:
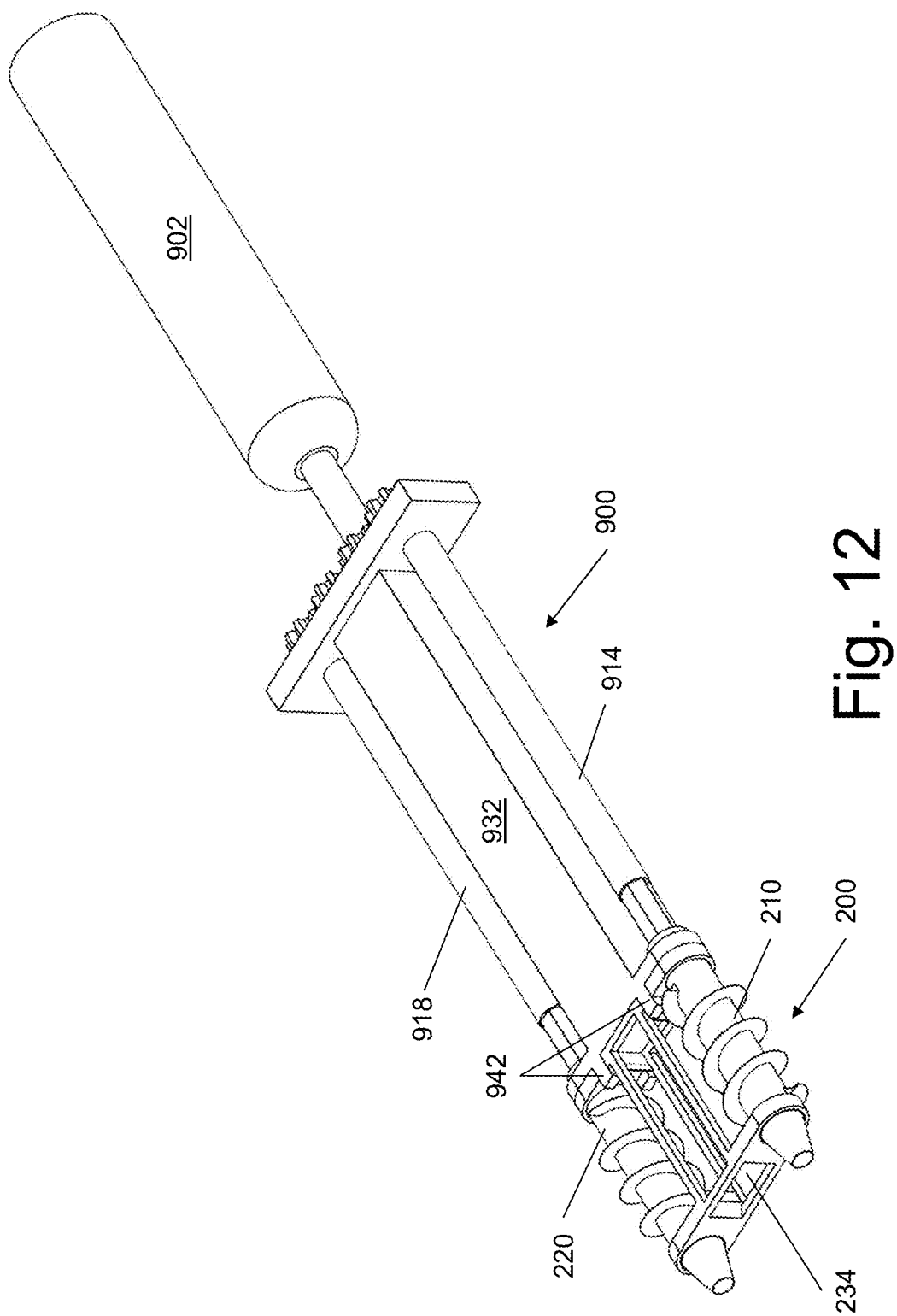
FIG. 12 is a perspective view of a system including an implant of FIG. 2A coupled to an insertion instrument of FIG. 9A.

Referring now to FIGS. 10 through 12, the manner of using one embodiment of the present invention will now be described. FIG. 10 is a flowchart illustrating a surgical method 1000 for inserting and positioning certain embodiments of the present invention. The method starts in step 1001 and flows to step 1002 where a surgical site is selected and prepared for insertion. In certain embodiments, a surgical site may be a facture between two boney structures. For example, FIG. 11A is a conceptual perspective illustration depicting a surgical site 1100 comprising two boney elements 1102 and 1104 which have been selected to be fused together. In FIG. 11A both boney elements 1102 and 1104 have been pre-drilled, indicated by bores 1106 and 1108. In other embodiments, drilling of the bores 1106 and 1108 may not be necessary. In this illustrative embodiment, the diameter of the bores 1106 and 1108 are undersized relative to the shaft diameters of the propulsors in the implant to be inserted.

FIG. 11B is a conceptual perspective illustration of the surgical site 1100 illustrating where a bone saw was also used to resect a small area 1110 between the bores 1106 and 1108 which may be used as an insertion channel for various embodiments of the medical implants described above. In certain embodiments, resection may not be necessary or desirable. In certain situations, the resection is undersized relative to the chassis height of the medical implant.

In other situations, there may be a gap (not shown) between the boney elements 1102 and 1104 of the surgical site 1100. In such situations, passive or active compression techniques may be used to close the gap between the boney structures as discussed above.

Referring back to FIG. 10, in step 1004, an implant, such as implant 200 (described above) may be coupled to the insertion instrument 900 as illustrated in FIG. 12. In certain embodiments, the coupling may be made during the manufacturing process if the insertion instrument 900 is designed to be a single use instrument packed in a sterile container. If the insertion instrument is designed to be a multi-use instrument, then the implant 200 may be coupled to the insertion instrument 900 prior to insertion and after the selection of the desired size of the implant. As one skilled in the art would recognize, the distance between the centers of the bores 1106 and 1108 should be roughly the same as the distance between the longitudinal axes of the propulsors of the selected medical implant.

Once the medical implant is coupled to the insertion instrument, in step 1006, the insertion instrument can then be aligned and introduced into the bores 1106 and 1108 of the surgical site 1100 (in embodiments where pre-drilled bores are necessary or required). In certain embodiments, surgical guidewires may be used to assist in guiding the implant to the desired location. Once aligned, the user may actuate the propulsors within the implant (step 1008) by turning the handle 902 relative to the mounting unit 932 (FIG. 12). As explained above, the rotation of the handle 902 will cause the first secondary shaft 914 to rotate in one direction and will also cause the second secondary shaft 918 to rotate in an opposite direction. In turn, the rotation of the first secondary shaft 914 will induce a torque and/or rotation by the propulsor 210 (See FIG. 2B) in the first direction. Similarly, the rotation of the second secondary shaft 918 will induce a torque and/or rotation by the propulsor 220 (See FIG. 2A) in the opposite direction.

As explained in reference to FIGS. 1D and 2D above, the respective rotations of the propulsors 210 and 220 will propel the medical implant 200 into the boney structures until the medical implant reaches the desired location. If for some reason, the medical implant 200 needs to be repositioned during the surgical procedure, the user can turn the handle 902 in an opposite direction—which will cause the implant to reverse direction within the boney tissue so that exact positioning can occur.

As also explained above in reference to FIG. 2D, as the medical implant 200 moves forward through the boney tissue, the tissue entering through the mouth 232 and the tissue entering through the sides by the rotation of the flights 214 and 224 "self-fill" the retaining cavity 234 with local tissue graft material and compresses harvested material within the retaining cavity 234 (step 1010).

In certain embodiments with passive or active compression features, such as the embodiments discussed above in reference to FIGS. 5A and 6A, the forward movement of the implant 200 through the boney tissue may also cause compression between the boney elements 1102 and 1104 (step 1012). In situations where there is a gap between the boney structures, such compression features may close the gap between the boney structures.

Once the medical implant 200 is in the desired location, in step 1014, the medical implant 200 may be decoupled from the insertion instrument 900. In certain embodiments the decoupling may entail pulling on the insertion instrument 900 with enough force to overcome the retaining force on the implant 200 provided by the retaining fingers 942 (see also FIGS. 9A-9D). In step 1016, the surgical site can then be closed in a traditional manner and the process finishes in step 1018.

ADVANTAGES

As can be seen from the above discussion, there is an active relationship between the various embodiments of the chasses and propulsors that causes the various embodiments to be able to be inserted without the use of impaction.

During implant insertion, the action of the propulsor's rotation compresses the boney elements together. This compression in turn produces a material boney element alignment. Furthermore, in certain embodiments, the rotation of the propulsors forces the implant to actively harvest graft into the implant's graft chamber. Continued rotation of the flight of each propulsor also compresses the graft material within this chamber. Furthermore, in certain embodiments, the angular momentum of the flights channels compressed material between and within the flight element itself.

The various embodiments described here may be used anywhere in the body for joining or fixating one or more boney elements, such as but not limited to joint spaces, a break resultant from trauma, a break resultant from iatrogenic action, or across or within a singular bone which needs to be stabilized or strengthened.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112(f). Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC 112(f).

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

What is claimed is:

1. A surgical implant comprising:
   a chassis comprising,
      a main body positioned along a longitudinal axis;
      a first arm extending laterally from a side of the main body having a first bearing aperture defined therein;
      a second arm extending laterally from the main body on an opposing side of the main body, the second arm having a second bearing aperture defined therein;
   a first propulsor comprising,
      a first longitudinal shaft having a first rotational axis;
      a clockwise auger flight positioned about a portion of the first longitudinal shaft,
      a first smooth bearing portion of the first longitudinal shaft;
      wherein the first smooth bearing portion fits within the first bearing aperture;
      wherein the first longitudinal shaft is positioned a first lateral distance from the main body of the chassis such that a rotation of the clockwise auger flight clears the main body;
   a second propulsor comprising,
      a second longitudinal shaft having a second rotational axis;
      a counter-clockwise auger flight positioned about a portion of the second longitudinal shaft,
      a second smooth bearing portion of the second longitudinal shaft;

wherein the second smooth bearing portion fits within the second bearing aperture; and wherein the second longitudinal shaft is positioned a second lateral distance from the main body of the chassis such that a rotation of the counter-clockwise auger flight clears the main body; and wherein the first rotational axis is a same plane as the second rotational axis.

2. The surgical implant of claim 1, wherein the chassis further comprises:

a third arm extending laterally from the main body having a third bearing aperture defined therein;

a fourth arm extending laterally from the main body having a fourth bearing aperture defined therein and extending in opposite direction from the third arm;

wherein the first bearing aperture is linearly aligned with the third bearing aperture and the second bearing aperture is linearly aligned with the fourth bearing aperture;

a third smooth bearing portion on the first shaft of the first propulsor, wherein the third smooth bearing portion fits within the third bearing aperture; and a fourth smooth bearing portion on the second shaft of the second propulsor, wherein the fourth smooth bearing portion fits within the fourth bearing aperture.

3. The surgical implant of claim 1, wherein the main body comprises a cage having a distal face and a proximal face, wherein the distal face defines an aperture for receiving bone tissue.

4. The surgical implant of claim 3, wherein the distal face comprises at least one member having a distal face which is shaped to cut through boney tissue during positioning.

5. The surgical implant of claim 1, wherein the main body comprises a cage having at least one side aperture for receiving bone tissue from a cutting action of at least one propulsor.

6. The surgical implant of claim 1, wherein the main body comprises a flexible region that can be biased before implantation to actively compress boney tissue after implantation.

7. The surgical implant of claim 6, wherein the flexible region is formed from an elastomeric material.

8. The surgical implant of claim 6, wherein the flexible region is formed from a shape memory alloy.

9. The surgical implant of claim 6, wherein the flexible region is a mechanical linkage.

10. The surgical implant of claim 1, wherein the chassis is fenestrated to encourage bone growth after placement.

11. The surgical implant of claim 1, wherein the chassis is cannulated.

12. The surgical implant of claim 1, wherein each propulsor comprises a distal end and a proximal end and the distal end is pointed to cut through boney tissue during positioning.

13. The surgical implant of claim 1, wherein each propulsor comprises a distal end and a proximal end and the distal end including a cutting surface to cut through boney tissue during positioning.

14. The surgical implant of claim 1, wherein each propulsor comprises a distal end and a proximal end and the proximal end includes a torque engagement feature.

15. The surgical implant of claim 1, wherein each propulsor comprises a distal end and a proximal end, wherein the distal end includes a forward distal thread-form shape to assist in drilling through boney tissue during implant positioning.

16. The surgical implant of claim 1, wherein the longitudinal axis of the first shaft of the first propulsor and the longitudinal axis of the second shaft of the second propulsor intersect at a common point forward to the implant.

17. The surgical implant of claim 1, wherein the longitudinal axis of the first shaft of the first propulsor and the longitudinal axis of the second shaft of the second propulsor intersect at a common point behind the implant.

18. The surgical implant of claim 1 wherein each propulsor is fenestrated to encourage bone growth after placement.

19. The surgical implant of claim 1 wherein each propulsor is cannulated.

* * * * *